United States Patent
Tischendorf et al.

(10) Patent No.: US 10,433,737 B2
(45) Date of Patent: Oct. 8, 2019

(54) MEDICAL DEVICE INCLUDING FEEDTHROUGH ASSEMBLY

(71) Applicant: Medtronic, Inc., Minneapolis, MN (US)

(72) Inventors: Brad C. Tischendorf, Minneapolis, MN (US); Christian S. Nielsen, River Falls, WI (US)

(73) Assignee: Medtronic, Inc., Minneapolis, MN (US)

( * ) Notice: Subject to any disclaimer, the term of this patent is extended or adjusted under 35 U.S.C. 154(b) by 304 days.

(21) Appl. No.: 15/418,265

(22) Filed: Jan. 27, 2017

(65) Prior Publication Data

US 2018/0214032 A1 Aug. 2, 2018

(51) Int. Cl.
| | |
|---|---|
| *H01M 10/052* | (2010.01) |
| *A61B 5/0215* | (2006.01) |
| *A61B 5/00* | (2006.01) |
| *A61B 5/0402* | (2006.01) |
| *A61B 5/07* | (2006.01) |
| *A61N 1/05* | (2006.01) |

(52) U.S. Cl.
CPC .......... *A61B 5/0215* (2013.01); *A61B 5/0402* (2013.01); *A61B 5/076* (2013.01); *A61B 5/6869* (2013.01); *A61N 1/0587* (2013.01); *A61B 2560/0214* (2013.01); *A61B 2562/12* (2013.01)

(58) Field of Classification Search
CPC ........................ H01M 10/052; H01M 10/0525
See application file for complete search history.

(56) References Cited

U.S. PATENT DOCUMENTS

| | | | |
|---|---|---|---|
| 4,309,507 A | 1/1982 | Davis et al. | |
| 4,349,692 A | 9/1982 | Davis et al. | |
| 6,498,951 B1 | 12/2002 | Larson et al. | |
| 6,622,046 B2 | 9/2003 | Fraley et al. | |
| 6,721,602 B2 * | 4/2004 | Engmark ............... | A61N 1/375 607/36 |
| 8,129,622 B2 | 3/2012 | Taylor et al. | |
| 8,288,654 B2 | 10/2012 | Taylor et al. | |
| 8,519,280 B2 | 8/2013 | Teske | |

(Continued)

OTHER PUBLICATIONS (PCT/US2018/014355) PCT Notification of Transmittal of the International Search Report and the Written Opinion of the International Searching Authority, dated Jun. 1, 2018, 13 pages.

*Primary Examiner* — Olatunji A Godo

(57) ABSTRACT

In some examples, an implantable medical device (IMD) comprises an electrochemical cell compartment that may define a barrier between an inside of the compartment and an outside of the compartment. The IMD may include an electrically conducting pad. The IMD may comprise an electrically conducting pin coupled to the pad. The pad may include top and bottom sides. The pin may extend from the bottom side of the pad. The pad may be positioned outside of the compartment and the pin may extend through an aperture in the compartment from inside the compartment to pad positioned outside of the electrochemical cell compartment. The IMD may include an electrically insulating material surrounding the aperture and between the bottom side of the pad and the compartment. The insulating material may insulate the pad from the barrier and form a seal between the inside of the compartment and the outside of the compartment.

32 Claims, 14 Drawing Sheets

(56) References Cited

U.S. PATENT DOCUMENTS

| | | |
|---|---|---|
| 8,569,633 B2 | 10/2013 | Receverur et al. |
| 8,751,002 B2 | 6/2014 | Kast et al. |
| 8,864,676 B2 | 10/2014 | Beasley et al. |
| 9,132,268 B2 | 9/2015 | Receverur et al. |
| 9,278,223 B2 | 3/2016 | Kast et al. |
| 9,345,895 B2 | 5/2016 | Iyer et al. |
| 2004/0191621 A1 | 9/2004 | Heller |
| 2004/0260354 A1 | 12/2004 | Nielsen et al. |
| 2006/0221543 A1* | 10/2006 | Stevenson ............... H01G 4/232 361/302 |
| 2006/0247714 A1 | 11/2006 | Taylor et al. |
| 2007/0060970 A1 | 3/2007 | Burdon et al. |
| 2007/0254212 A1* | 11/2007 | Viavattine .............. A61N 1/375 429/164 |
| 2009/0229858 A1 | 9/2009 | Taylor et al. |
| 2012/0270330 A1 | 10/2012 | Tao et al. |
| 2013/0131744 A1 | 5/2013 | Viavattine |
| 2013/0286536 A1 | 10/2013 | Iyer et al. |
| 2014/0276928 A1 | 9/2014 | Vanderpool et al. |
| 2015/0045862 A1 | 2/2015 | Goldman et al. |
| 2016/0233656 A1 | 8/2016 | Thom |
| 2016/0260938 A1 | 9/2016 | Nielsen et al. |

\* cited by examiner

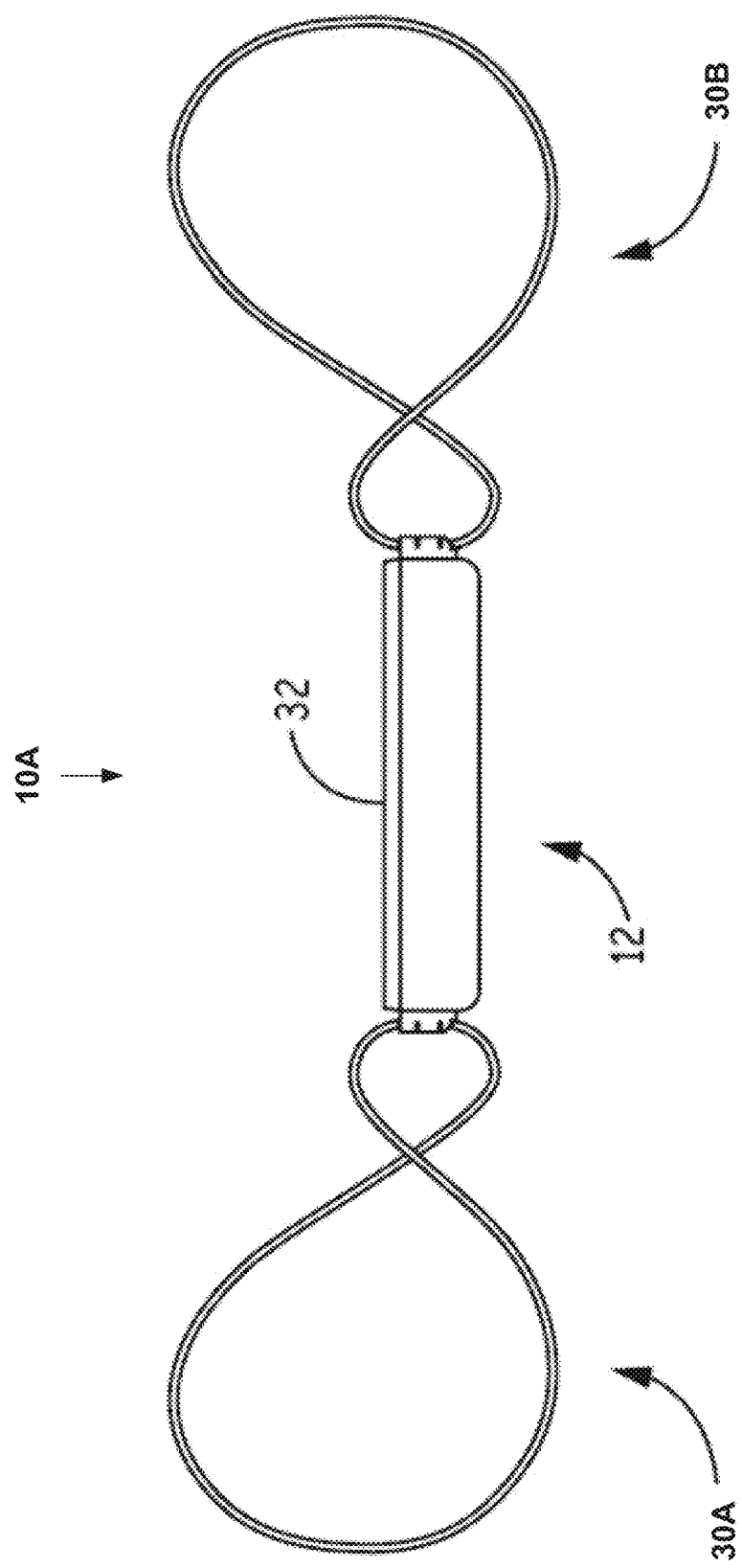

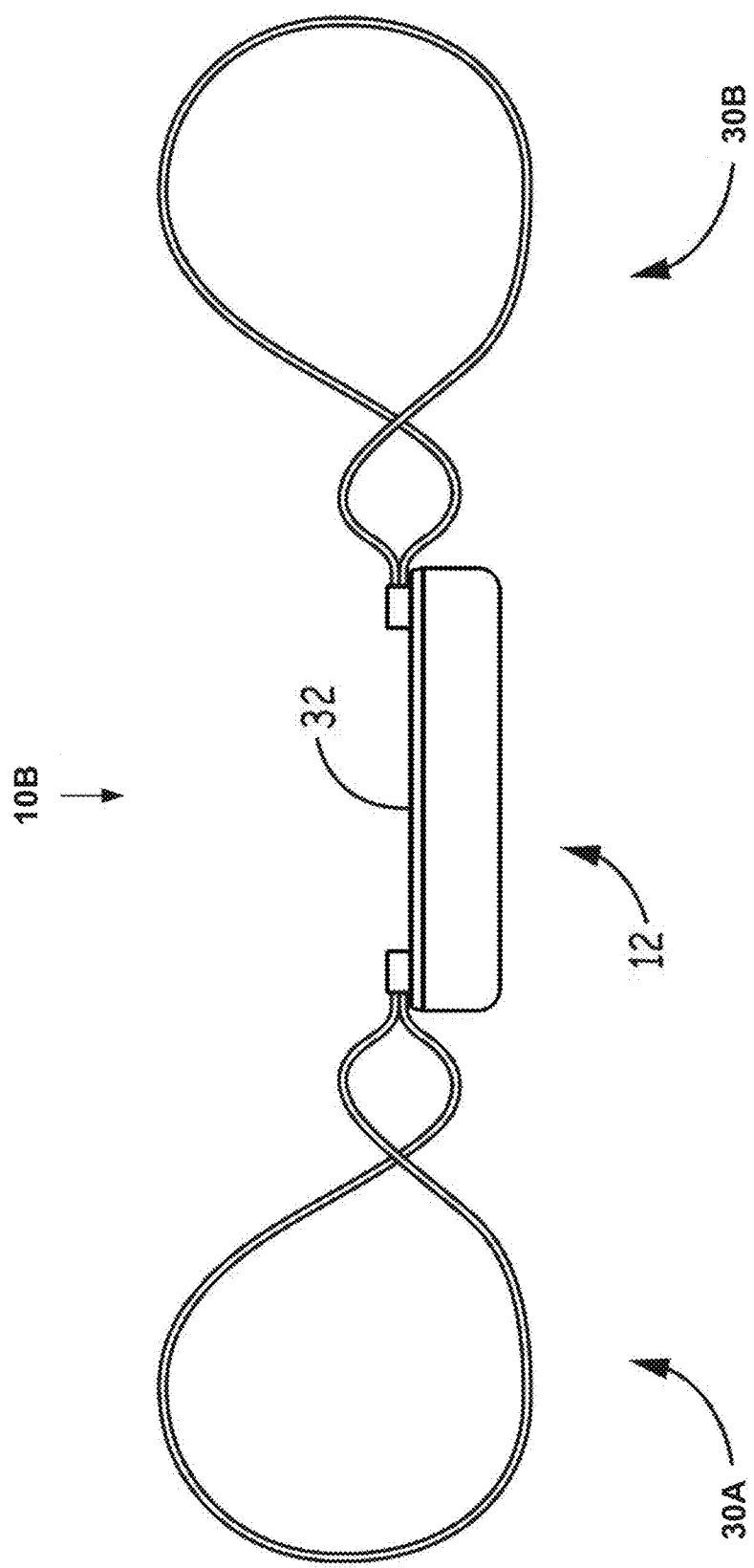

MEDICAL DEVICE INCLUDING FEEDTHROUGH ASSEMBLY

TECHNICAL FIELD

The disclosure relates generally to medical devices and, more particularly, medical devices including feedthrough assemblies.

BACKGROUND

Various implantable medical devices (IMDs) have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable medical devices capable of therapeutic as well as diagnostic functions such as pacemakers, cardioverters, defibrillators, biochemical sensors, and pressure sensors, among others. Such devices may be associated with leads to position electrodes or sensors at a desired location, or may be leadless, with the ability to wirelessly transmit data either to another device implanted in the patient or to another device located externally of the patient, or both.

By way of illustrative example, implantable miniature sensors have been proposed and used in blood vessels to measure directly the diastolic, systolic, and mean blood pressures, as well as body temperature and cardiac output. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. If linked electronically to another implanted therapeutic device (e.g., a pacemaker), the data may be used to facilitate control of that device. Such sensors also, or alternatively, may be wirelessly linked to an external receiver.

Size may be an important factor in the design of medical devices implanted into the body of the patient. Likewise, size may be an important factor in the design of components within IMDs.

SUMMARY

In some aspects, the disclosure is directed to medical devices, such as IMDs, including feedthrough assemblies, and techniques for manufacturing and operating the same. The feedthrough assembly may electrically connect an electrochemical cell of a medical device across a substrate physically separating the electrochemical cell within a cell compartment to another component outside the cell compartment. For example, the feedthrough assembly may electrically connect an electrochemical cell within the cell compartment to electronics of the medical device located outside the compartment. The electrical connection between the electronics of the medical device to the electrochemical cell via the feedthrough assembly may allow for the electrochemical cell to provide operational power to the electronics while also providing a hermetically sealed cell compartment containing the electrochemical cell. In some examples, the feedthrough may electrically couple the electrochemical cell to components other than electronics of the medical device, e.g., by providing an electrical connection to a component outside the outer housing of the medical device.

In one example, the IMD includes an electrochemical cell compartment (e.g., a battery compartment). The compartment may define a barrier between an inside and an outside of the electrochemical cell compartment. The IMD may include an electrically conducting pin coupled to an electrically conducting pad. In one example, the pad includes a top side and a bottom side. The pin may extend from the bottom side of the electrically conducting pad. The pad may be positioned outside of the electrochemical cell compartment, and the pin may extend through an aperture in the compartment from inside the electrochemical cell compartment to the electrically conducting pad positioned outside of the electrochemical cell compartment.

In some examples, an electrically insulating material may surround the aperture and the electrically insulating material may be between the bottom side of the electrically insulating pad and the electrochemical cell compartment. The electrically insulating material may be configured to insulate the electrically conducting pad from the barrier, and may be configured to form a seal between the inside of the electrochemical cell compartment and the outside of the electrochemical cell compartment. The seal may be a hermetic seal. In some examples, the electrically insulating material is positioned within at least a portion of the aperture in the electrochemical cell compartment. In other examples, the aperture is substantially vacant of the electrically insulating material.

In one example, the feedthrough assembly may include an electrically conducting pad positioned within the electronic compartment and an electrically conducting pin electrically coupled to the conducting pad. The conducting pin may extend from the conducting pad through the aperture in the substrate to access the electrochemical cell, e.g., to couple the pin to a polarity of the electrochemical cell. An insulating material (e.g., an electrically insulating material such as a frit or a plastic) may be disposed on the substrate such that the insulating material is positioned between the electrically conducting pad and the adjacent surface of the cover portion and also positioned within at least a portion of the aperture of substrate between the pin extending through the aperture. In one example, the insulating material includes a glass frit, such as may be used for a glass frit hermetic feedthrough, or an electrically insulating polymer material. In an example, the frit may be the form of glass prior to sealing portions of the feedthrough assembly together. In an example, the frit may start as a powder, and may be a monolithic piece of material after sealing. In an example, frit may refer to the material used to create a seal, such as at different stages in the manufacturing of the seal (e.g., base materials, materials during manufacture, or final product). As such, frit may comprise a low temperature reflow at, in an example, a point in time before the frit is sealed. As will be described herein, the feedthrough assembly may provide for a hermetically sealed electrochemical cell compartment while also providing a relatively low profile feedthrough configuration.

In one example, the disclosure is directed to a method for manufacturing an implantable medical device including electrochemical cell compartment that may define a barrier between an inside of the electrochemical cell compartment and an outside of the electrochemical cell compartment. The method may comprise positioning an electrically conducting pin to extend through an aperture in the electrochemical cell compartment. The electrically conducting pin may be coupled to an electrically conducting pad including a top side and a bottom side. The electrically conducting pad may be positioned outside of the electrochemical cell compartment. The method may comprise disposing an electrically insulating material to surround the aperture and be between the bottom side of the electrically conducting pad and the electrochemical cell compartment. The electrically insulating material may be configured to insulate the electrically conducting pad from the barrier and may form a seal between the inside of the electrochemical cell compartment and the outside of the electrochemical cell compartment.

In one aspect, the disclosure is directed to an implantable medical device comprising: an outer housing; an electrochemical cell compartment within the outer housing; an electronics compartment within the outer housing; a cover portion positioned between the electrochemical cell compartment and the electronics compartment within the outer housing, the cover portion including an aperture extending between the electrochemical cell compartment and the electronics compartment; a feedthrough including an electrically conducting pad coupled to an electrically conducting pin, the electrically conducting pin extending through the aperture, the electrically conducting pad positioned outside of the electrochemical cell compartment and within the electronics compartment within the outer housing; and an electrically insulating material disposed on the cover portion and within at least a portion of the aperture, the electrically insulating material positioned between the electrically conducting pad and the cover portion, the electrically insulating material positioned within the aperture between the electrically conducting pin and a perimeter of the aperture to electrically insulate the electrically conducting pin from the cover portion, and the electrically insulating material configured to separate the electrically conducting pad and the cover portion In another aspect, the disclosure is directed to a method for manufacturing an implantable medical device including an outer housing, an electrochemical cell compartment within the outer housing, and an electronics compartment within the outer housing, the method comprising: positioning a feedthrough including an electrically conducting pad coupled to an electrically conducting pin such that the electrically conducting pin extends through an aperture in a cover portion, wherein the cover portion is configured to be positioned between the electrochemical cell compartment and the electronics compartment within the outer housing and wherein positioning the feedthrough includes positioning the electrically conducting pad outside of the electrochemical cell compartment and within the electronics compartment within the housing; and disposing an electrically insulating material on the cover portion and within at least a portion of the aperture, the electrically insulating material positioned within the aperture between the electrically conducting pin and a perimeter of the aperture to electrically insulate the electrically conducting pin from the cover portion, and the insulating material separating the electrically conducting pad and the cover portion.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIGS. 2A and 2B are diagrams illustrating side profile views of example sensor assemblies.

DETAILED DESCRIPTION

Figure 1A:
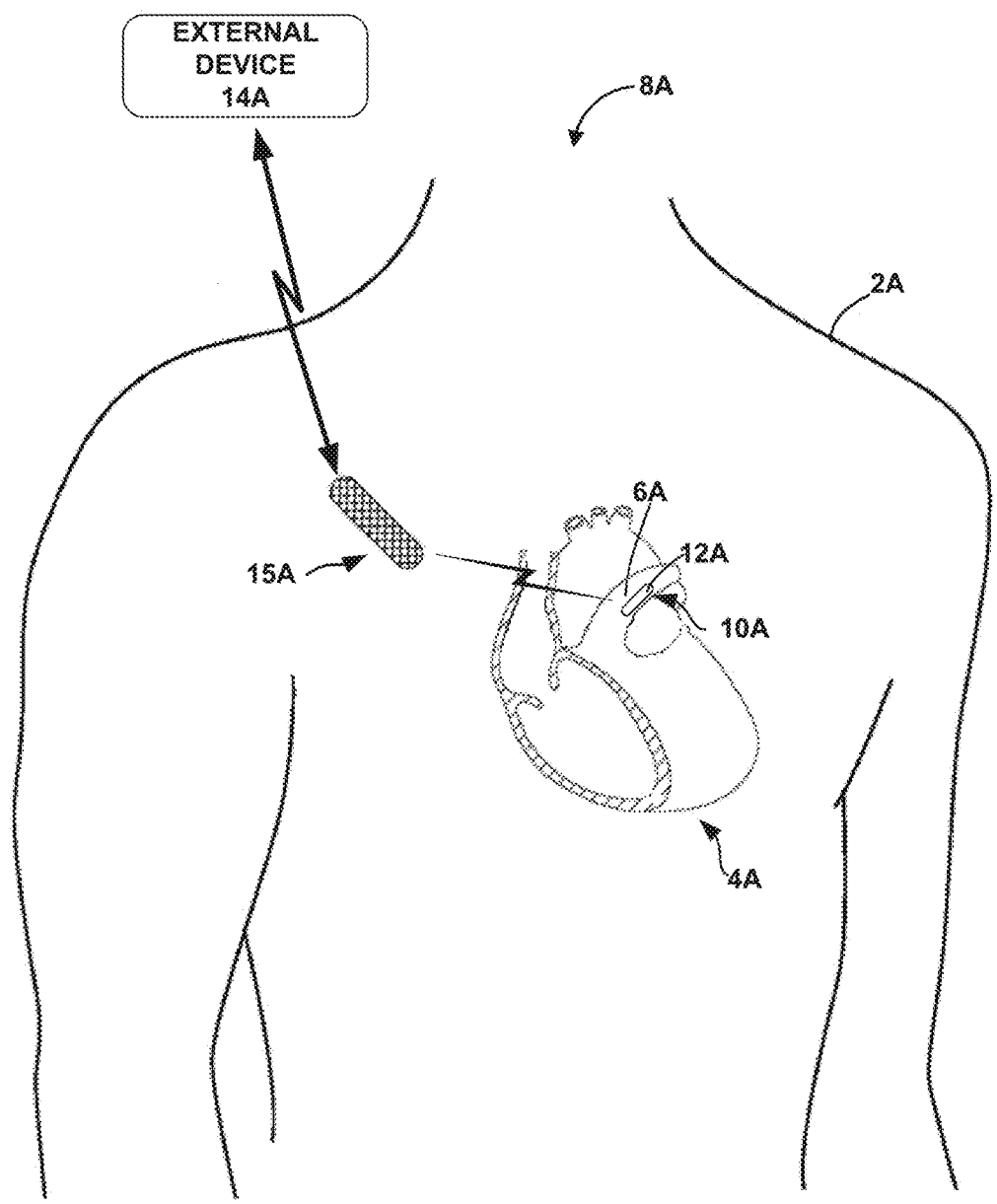
FIG. 1A is a conceptual diagram illustrating an example of a patient with implanted medical devices, including a sensor assembly, in accordance with one example according to this disclosure.

The disclosure describes examples of medical devices including one or more batteries or other electrochemical cells that supplies operational power to the device (e.g., operational power to the device electronics) and/or supplies an electric signal to a component outside a cell compartment in which the electrochemical cells is contained via a feedthrough. In some examples, the medical devices that may include miniaturized implantable medical devices configured to sense various physiological parameters of a patient, such as one or more physiological pressures. Such devices may include a hermetic housing that contains a battery and electronics. In an example, this disclosure describes a cost effective electrical feedthrough including an electrically conducting pad (e.g., an interconnection pad) and conductive pin with minimal use of internal volume of the implantable medical device while providing for an electrical connection between the battery and electronics across a hermetically sealed battery compartment (also referred to as an electrochemical cell compartment).

For ease of description, examples of the disclosure are described primarily with regard to medical devices including a feedthrough that electrically couples a battery or other electrochemical cell to electronics of the medical device located in another compartment outside the cell compartment containing the battery or other electrochemical cell. However, other examples are contemplated. For example, the feedthrough may be used to electrically couple the battery or other electrochemical cell to a component other than the electronics of the medical device contained in another compartment of the device or even a component located outside the outer housing of the device.

In an example, the medical device may employ a relatively thin walled structure, such as a micro battery for an implantable medical device (IMD). In an example, the medical device may employ a relatively small battery (e.g., the micro battery, a "very small battery," a battery that is smaller than normally used in IMDs). The medical device may employ features associated with such a battery that may be "thin," "small," "micro," or "sub-normal sized," and other components of the medical device may likewise be "thin," "small," "micro," or "sub-normal sized." In an example, the subject matter herein may refer to a glass frit hermetic feedthrough in an electrochemical cell (e.g., a micro battery).

For ease of description, examples of the present disclosure are primarily described with regard to miniaturized pressure sensing medical devices configured to be implanted within the heart of a patient. However, examples are not limited to such devices and configurations. Other medical devices including a battery electrically connected to electronics of the device via a feedthrough assembly are contemplated. In some examples, the electrical feedthrough may be employed with devices, batteries, and hermetic packages that may be, relative to implantable medical devices such as a pacemaker or defibrillator, normal sized or smaller than normal sized, such as where the low-profile construction (e.g., a "very" low profile construction, such as may be understood as much lower profiled relative to conventional constructions) of the electrical feedthrough may be advantageous. In some examples, the subject matter herein may be universally used for all battery types and hermetic packages. In some examples, for relatively larger cells or devices, the size of the features disclosed may not be as important compared to smaller cells or devices.

FIG. 1A illustrates exemplary medical device system 8A in conjunction with patient 2A. In the illustrated example, medical device system 8A includes an implantable medical device (IMD) 15A, which may comprise an implantable or insertable cardiac monitor or an implantable hub device, in communication with external device 14A. Medical device system 8A also includes implantable sensor assembly 10A, which comprises pressure sensing device 12A. As shown in FIG. 1A, implantable sensor assembly 10A may be implanted within pulmonary artery 6A of heart 4A. In some examples, pulmonary artery 6A of heart 4A may comprise a left pulmonary artery, whereas in other examples, pulmonary artery 6A may comprise a right pulmonary artery. For the sake of clarity, a fixation assembly for sensor assembly 10A is not depicted in FIG. 1A. A suitable fixation assembly configured to secure sensor assembly 10A within pulmonary artery 6A will be discussed below with respect to FIGS. 2A-4B.

In the illustrated example, IMD 15A comprises an insertable cardiac monitor (ICM) configured to sense and record cardiac electrogram (EGM) signals from a position outside of heart 4A, and will be referred to as ICM 15A hereafter. In some examples, ICM 15A includes or is coupled to one or more additional sensors, such as accelerometers, that generate one or more signals that vary based on patient motion, posture, blood flow, or respiration. ICM 15A may monitor a physiological parameter such as posture, heart rate, activity level, or respiration rate, and may do so at times when the one or more additional sensors, such as sensing device 12A, is measuring a patient parameter such as cardiovascular pressure. ICM 15A may be implanted outside of the thoracic cavity of patient 2A, e.g., subcutaneously or submuscularly, such as at the pectoral location illustrated in FIG. 1A. In some examples, ICM 15A may take the form of a Reveal LINQ™ ICM, available from Medtronic plc, of Dublin, Ireland.

Pressure sensing device 12A may be implanted within a pulmonary artery of patient 2A and may include pressure sensing circuitry configured to measure the cardiovascular pressure of patient 2A. Pressure sensing device 12A may utilize a feedthrough assembly in accordance with examples of the disclosure to electrically connect a battery or other electrochemical cell to electronics of the device to supply operation power to device 12A.

ICM 15A may transmit posture data, and other physiological parameter data acquired by ICM 15A, to external device 14A. ICM 15A also may transmit cardiovascular pressure measurements received from sensing device 12A to external device 14A. External device 14A may be a computing device configured for use in settings such as a home, clinic, or hospital, and may further be configured to communicate with ICM 15A via wireless telemetry. For example, external device 14A may be coupled to a remote patient monitoring system, such as Carelink®, available from Medtronic plc, of Dublin, Ireland. External device 14A may, in some examples, comprise a programmer, an external monitor, or a consumer device such as a smart phone.

External device 14A may be used to program commands or operating parameters into ICM 15A for controlling its functioning, e.g., when configured as a programmer for ICM 15A. External device 14A may be used to interrogate ICM 15A to retrieve data, including device operational data as well as physiological data accumulated in the memory of ICM 15A. The accumulated physiological data may include cardiovascular pressure generally, such as one or more of a systolic pressure, a diastolic pressure, and a mean pulmonary artery pressure, or medians of such pressures, although other forms of physiological data may be accumulated. In some examples, the interrogation may be automatic, e.g., according to a schedule. In other examples, the interrogation may occur in response to a remote or local user command. Programmers, external monitors, and consumer devices are examples of external devices 14A that may be used to interrogate ICM 15A.

Examples of wireless communication techniques used by ICM 15A and external device 14A include radiofrequency (RF) telemetry, which may be an RF link established via an antenna according to Bluetooth, WiFi, or medical implant communication service (MICS), or transconductence communication (TCC), which may occur via electrodes of ICM 15A. Examples of wireless communication techniques used by ICM 15A and pressure sensing device 12A may also include RF telemetry or TCC. In one example, ICM 15A and pressure sensing device 12A communicate via TCC, and ICM 15A and external device 14A communicate via RF telemetry.

Medical device system 8A is an example of a medical device system configured to monitor a cardiovascular pressure of patient 2A. Although not illustrated in the example of FIG. 1A, a medical device system may include one or more implanted or external medical devices in addition to or instead of ICM 15A and pressure sensing device 12A. For example, a medical device system may include a vascular ICD or pacemaker (e.g., IMD 15B illustrated in FIG. 1B), an extravascular ICD, or an intracardiac pacemaker. One or more such devices may generate physiological signals, and may include processing circuitry configured to monitor cardiovascular pressure. In some examples, the implanted devices may communicate with each other or with external device 14A.

Figure 1B:
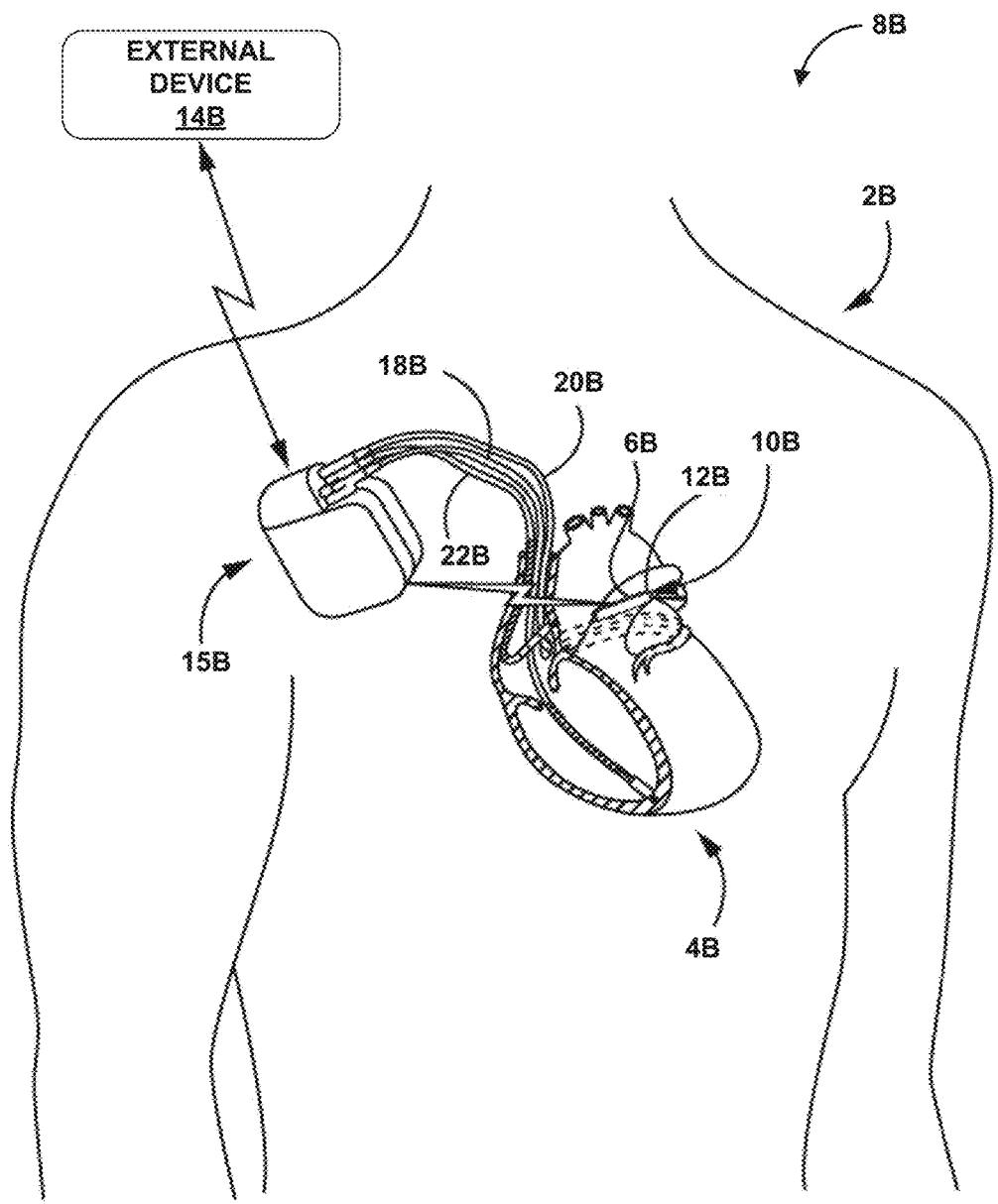
FIG. 1B is a conceptual diagram illustrating another example of a patient with implanted medical devices, including a sensor assembly, in accordance with one example according to this disclosure.

FIG. 1B illustrates, diagrammatically, a patient with implanted medical devices including a sensor assembly 10B implanted, for example, in the patient's left pulmonary artery 6B through which blood flows from heart 4B to the lungs, and another device, such as a pacemaker, defibrillator, or the like, referred to as IMD 15B. For purposes of this description, knowledge of cardiovascular anatomy is presumed and details are omitted except to the extent necessary or desirable to explain the context of the invention.

In some examples, IMD 15B may include one or more leads 18, 20, 22 that carry electrodes that are placed in electrical contact with selected portions of the cardiac anatomy in order to perform the functions of IMD 15B as is well known to those skilled in the art. For example, IMD 15B may be configured to sense and record cardiac EGM signals via the electrodes on leads 18B, 20B, 22B. IMD 15B may also be configured to deliver therapeutic signals, such as pacing pulses, cardioversion shocks, or defibrillation shocks, to heart 4B via the electrodes. In the illustrated example, IMD 15B may be a pacemaker, cardioverter, or defibrillator.

In some examples, this disclosure may refer to IMD 15B, particularly with respect to its functionality as part of a medical device system that monitors cardiovascular pressure and other physiological parameters of a patient 2B, as an implantable monitoring device or implantable hub device. In some examples, IMD 15B includes or is coupled to one or more additional sensors, such as accelerometers, that generate one or more signals that vary based on patient motion or posture, blood flow, or respiration. IMD 15B may monitor posture of patient 2B at or near the times when implantable pressure sensing device 12B is measuring cardiovascular pressure.

IMD 15B also may have wireless capability to receive and transmit signals relating to the operation of the device. IMD 15B may communicate wirelessly to an external device, such as external device 14B, or to another implanted device such as implantable pressure sensing device 12B of the sensor assembly 10B, e.g., as described above with respect to IMD 15A, external device 14A, and pressure sensing device 12A of FIG. 1A. In some examples, an implantable pressure sensing device 12 may communicate wirelessly and directly with an external device 14, rather than communicating with the external device 14 through the IMD 15.

Medical device system 8B is an example of a medical device system configured to monitor the cardiovascular pressure of patient 2B. One or more of IMD 15B, implantable pressure sensing device 12B, and external device 14B, individually, or collectively, may include processing circuitry that allows medical device system 8B to function as described herein. Such function may include measuring a cardiovascular pressure of patient 2B, such as PAP. In some examples, an implantable pressure sensing device 12 measures the cardiovascular pressure at a plurality of predetermined times during a day or a portion of a day, e.g. at night.

For the sake of clarity, a fixation assembly for sensor assembly 10B is not depicted in FIG. 1B. A suitable fixation assembly configured to secure sensor assembly 10B within pulmonary artery 6B will be discussed below with respect to FIGS. 2A-4B.

FIGS. 2A-4B illustrate example configurations of sensor assemblies 10 adapted for minimally invasive placement within a patient's blood vessel, the assembly being shown in its expanded, deployment configuration. Side profile views of the alternative examples of sensor assembly 10A and sensor assembly 10B (collectively "sensor assembly 10") are depicted in FIGS. 2A and 2B. Sensor assembly 10 includes pressure sensing device 12 coupled to fixation members 30A and 30B (collectively "fixation assembly 30"). Fixation assembly 30 and pressure sensing device 12 are arranged to enable sensor assembly 10 to be provided in a delivery configuration that may be navigated to an implant location, where it may be deployed into the deployment configuration. As described in this disclosure, it should be understood that the delivery configuration of sensor assembly 10 defines a pitch, width or diameter that is narrower along a common plane than the deployment configuration of sensor assembly 10.

Upon the release of sensor assembly 10 from a delivery device, such as a delivery catheter, fixation assembly 30 expands into the deployment configuration and comes into secure physical contact with the implant location of the wall of the blood vessel. In one example, fixation assembly 30 engages the interior wall of the vessel defining the blood flow lumen by exerting a sufficient outward expansion force to maintain sensor assembly 10 securely positioned at the implant location. In some examples, this may be achieved by configuring fixation assembly 30 to have a fully expanded configuration that includes a pitch, width, or diameter that is wider than that of the implant location of the blood vessel. Thus, fixation assembly 30 may remain inwardly biased by the implant location even when sensor assembly 10 is in the deployment configuration, such that fixation assembly 30 exerts the outward force necessary to maintain sensor assembly 10 at the implant location.

As illustrated in FIGS. 2A and 2B, pressure sensing device 12 may be attached to fixation assembly 30 in such a manner that sensing element 32 of pressure sensing device 12 may be maintained substantially away from the wall of the implant location when sensor assembly 10 is in the deployment configuration. It may be beneficial for sensing element 32 to be maintained in such a position for at least several reasons. For example, positioning sensing element 32 apart from the wall of the vessel lumen may permit full exposure of sensing element 32 to the blood flow of the vessel, and may prevent any obstruction of sensing element 32 that may be caused by the housing of sensor assembly 10 or by the vessel wall.

Figure 3A:
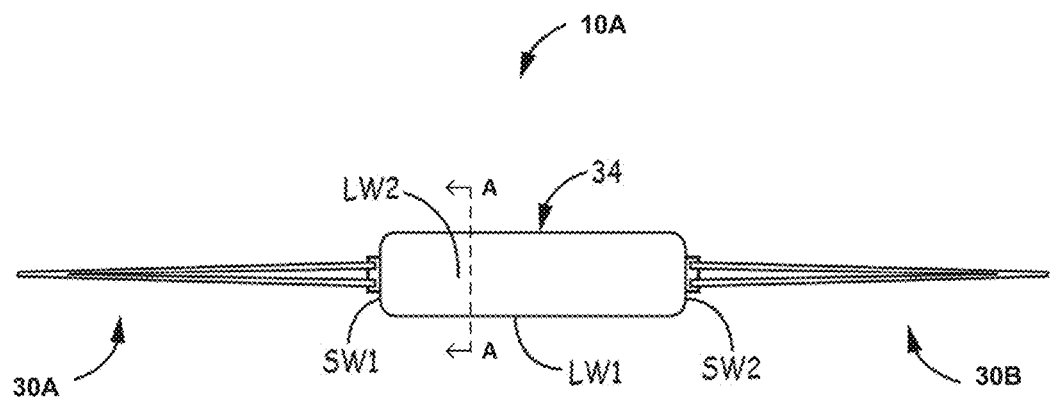
FIG. 3A is a diagram illustrating a bottom perspective view of the example sensor assembly of FIG. 2A.
Figure 3B:
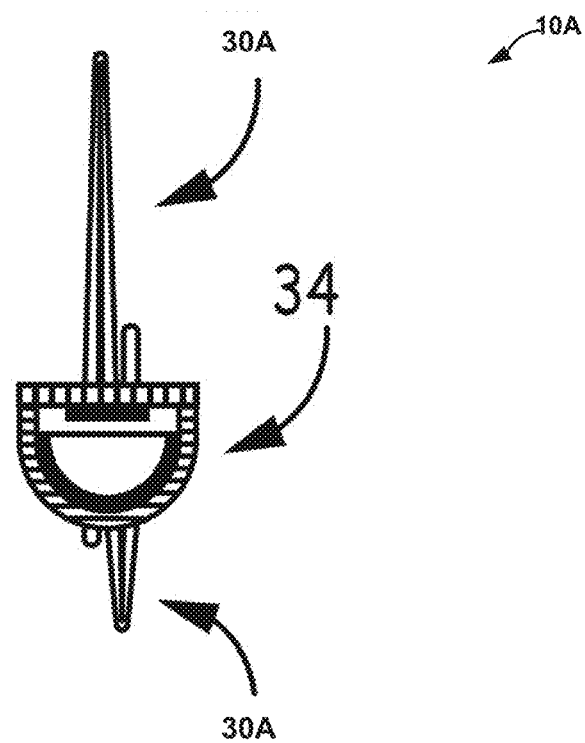
FIG. 3B is a diagram illustrating a side cross-sectional view of the example sensor assembly of FIG. 2A.

FIG. 3A illustrates a bottom perspective view of sensor assembly 10A. FIG. 3B illustrates a side cross-sectional view of sensor assembly 10A along cross-section A-A. Implantable pressure sensing device 12 of sensor assembly 10 includes capsule 34 that forms a hermetically sealed housing enclosing the operational components, such as the electronic circuitry or sensors, of sensor assembly 10. As will be described below, capsule 34 may also include a hermetically sealed electrochemical cell compartment (e.g., electrochemical cell compartment 160) that encloses a battery or other electrochemical cell to supply operational power to the operational components of assembly 10.

In the examples depicted, capsule 34 defines longitudinal walls LW1 and LW2 that extend from first lateral side wall SW1 to second lateral sidewall SW2. Longitudinal walls LW1 and LW2 define the longitudinal axis of pressure sensing device 12. As will be described in further detail with respect to reference FIG. 4, fixation members 30A and 30B are coupled to an exterior of capsule 34. In some examples, such as the example illustrated in FIG. 3A, fixation members 30A and 30B are depicted as being coupled to first lateral sidewall SW1 and second lateral sidewall, SW2, respectively.

Figure 4A:
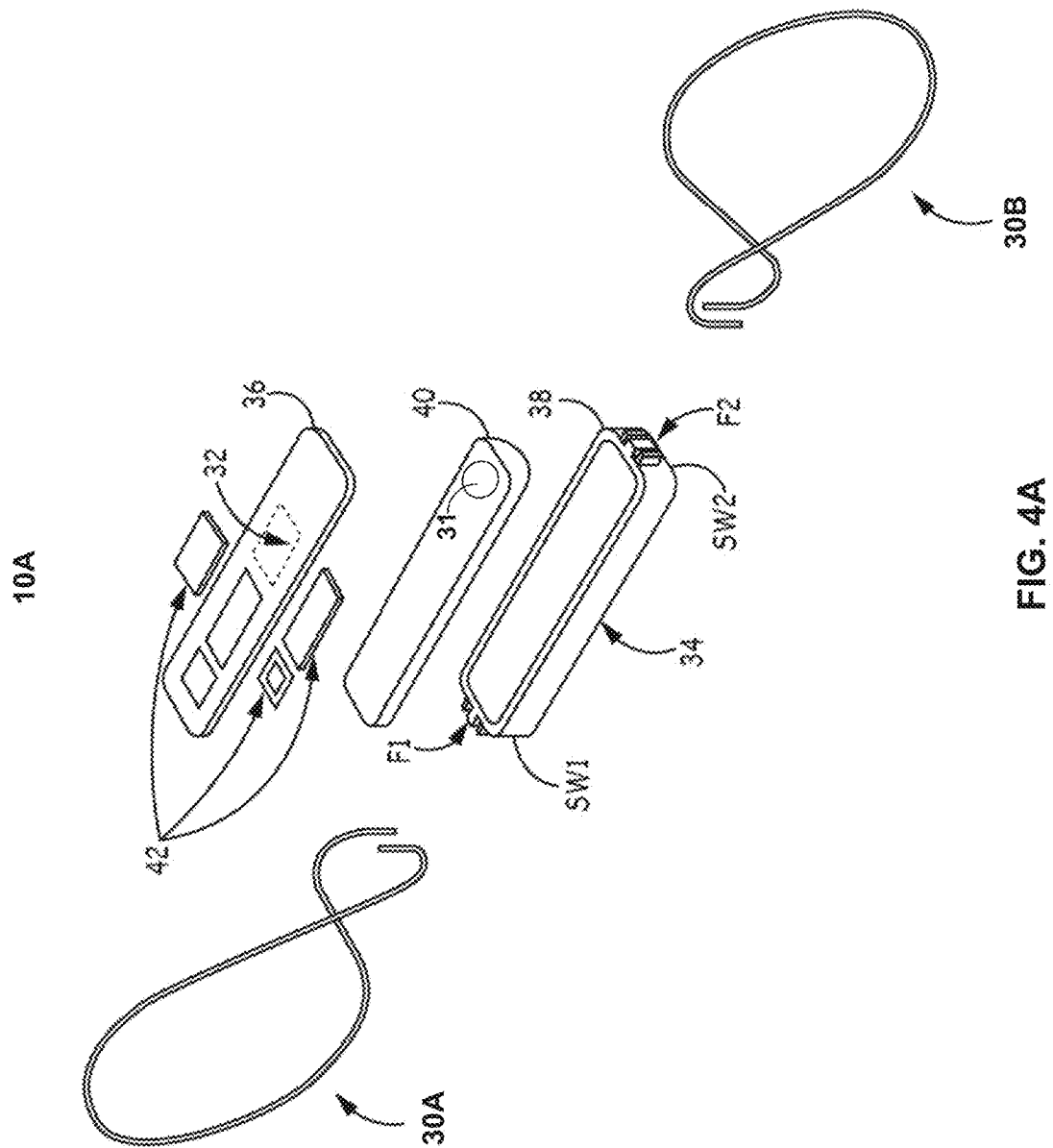
FIG. 4A is a diagram illustrating an exploded perspective view of the example sensor assembly of FIG. 2A.
Figure 4B:
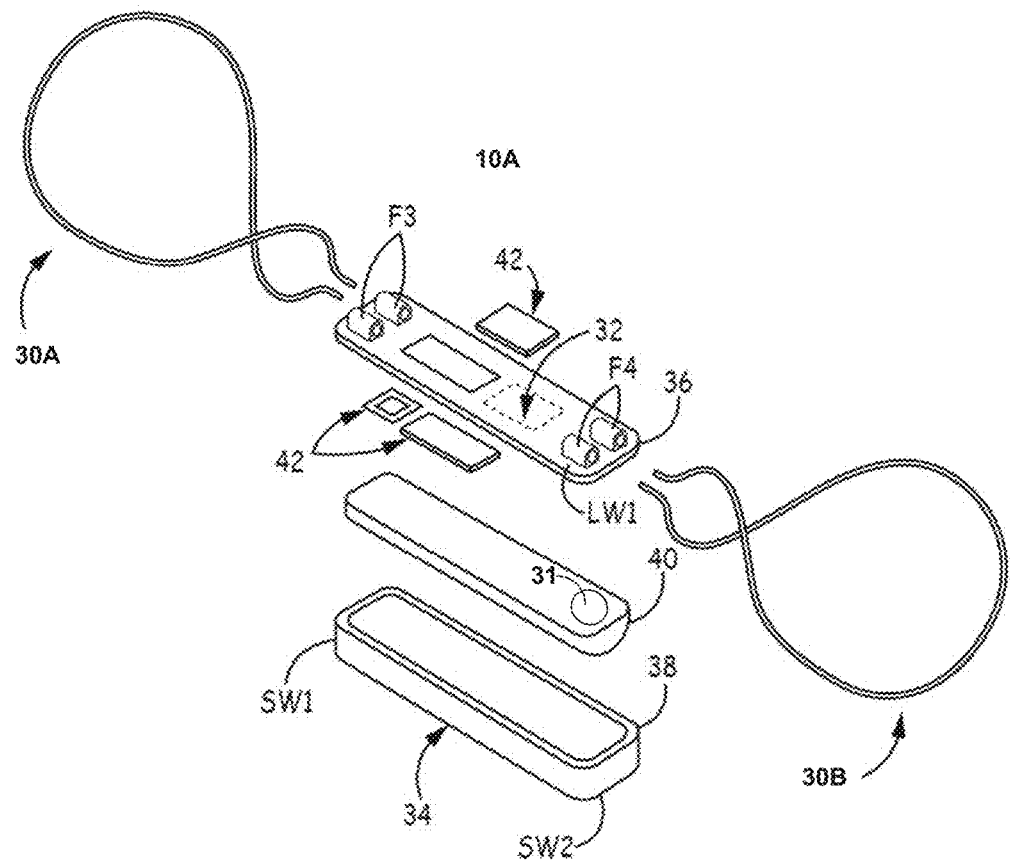
FIG. 4B is a diagram illustrating an exploded perspective view of the example sensor assembly of FIG. 2B.

FIGS. 4A and 4B are exploded perspective views of sensor assemblies 10A and 10B, respectively in accordance with some example configurations. In the examples shown, capsule 34 may include an elongate body that defines an interior cavity. The interior cavity of capsule 34 may be of suitable shape and proportion to contain battery 40, as well as electronics and sensor components 42, of pressure sensing device 12. Preferably, capsule 34 comprises a shape that is easily accepted by the patient's body while causing minimum discomfort. For example, the body of capsule 34 may be formed in a cylindrical shape with cylindrical sidewalls. However, non-cylindrical configurations may be employed, such as substantially rectangular or other configurations. In any configuration, it is preferred that the corners and edges of capsule 34 comprise radii of sufficient size to impart smoothly contoured surfaces. For example, the body of capsule 34 depicted in FIG. 4A is formed as a generally rectangular structure having edges and corners that are contoured as described.

In some examples, capsule 34 comprises two sections, such as section 36 and section 38, as shown in FIG. 4A. As depicted, section 36 may contain sensing element 32, which in some examples may comprise a pressure sensing diaphragm or other element configured to sense pressure, while section 38 may contain the battery 40 and electronics and sensor components 42. However, in other examples, capsule 34 may comprise fewer than two sections or more than two sections, and the distribution of battery 40 and electronics and sensor components 42 may vary. As described further below, capsule 34 may include an electrochemical cell compartment separated from other portions of capsule 34, such as, e.g., an electronics compartment containing electronics of device 10A. A feedthrough assembly may be employed to electrically couple the battery or other electrochemical cell contained by the electrochemical cell compartment to the electronics of the device through a wall of the electrochemical cell compartment while providing a hermetically sealed cell compartment. As shown in FIGS. 4A and 4B, devices 10A and 10B each may include feedthrough assembly 31. Feedthrough assembly 31 may allow for an electrical connection between battery 40 or other electrochemical cell to electronics the electronics (e.g., processing circuitry and sensor components 42) of the devices across a portion of the compartment containing the battery 40 to supply operation power to the devices while also hermetically sealing the battery compartment. Feedthrough assembly 31 may have a relatively low profile that fits within the relative small size of capsule 34.

Capsule 34 may be formed from one or more biocompatible materials that are capable of being hermetically sealed when sections 36 and 38 are joined. A number of such biocompatible materials may be employed, as will be understood by those familiar with the art, including metals and biocompatible plastics. For example, sections 36 and 38 may be formed from unalloyed titanium, such as unalloyed titanium having an American Society for Testing and Materials (ASTM) grade 1 to grade 4. In other examples, sections 36 and 38 may be formed from an alloyed titanium including aluminum and vanadium, in which case ASTM grade 5 may be preferred. For examples in which sections 36 and 38 comprise a metal, the metal material may optionally be selected for compatibility with fixation assembly 30 material, thereby permitting secure coupling of fixation assembly 30 to capsule 34. In other examples, capsule 34 and fixation assembly 30 may be integrally formed from one or more of the same or distinct materials. In some examples, capsule 34, in addition to or instead of some portions of fixation member 30, may be encapsulated in a biologically inert material. A suitable biologically inert material may comprise a dielectric barrier material, such as a film of silicone or poly(p-xylylene) polymer, the latter of which may be sold under the trademark PARYLENE.

As shown in FIG. 4A, capsule 34 may include fasteners F1 and F2 that define channels configured to receive a segment of fixation assembly 30. A similar configuration is depicted in FIG. 4B, wherein capsule 34 may include fasteners F3 and F4 that also are configured to receive a segment of the fixation assembly 30. In some examples, the segment of fixation assembly 30 received by fasteners F1-F4 may include a portion along a length of fixation assembly 30, or may include a free end of fixation assembly 30. Fasteners F1-F4 may be coupled to an exterior surface of capsule 34, or in alternative examples, may be formed integrally with capsule 34. For example, as shown in the example of FIG. 4A, fasteners F1 and F2 are provided at lateral sidewalls SW1 and SW2, respectively. In the alternative example of FIG. 4B, fasteners F3 and F4 are provided at opposing locations on longitudinal wall LW2.

In some examples, fasteners F1-F4 may be configured as pairs of tabs and arranged to define one or more channels for receiving one or more segments of fixation assembly 30. Each of fasteners F1-F4 may include a pair of tabs that are aligned longitudinally as described, for example, in U.S. Pat. No. 8,864,676 to Beasley et al., which is incorporated herein by reference in its entirety. In some examples, fasteners F1-F4 may be coupled to capsule 34 through welding or another suitable joining technique. Alternatively, fasteners F1-F4 may be formed integrally with capsule 34. In any case, fasteners F1-F4 may preferably be disposed on opposing ends of capsule 34, although other configurations of fasteners F1-F4 are within the scope of this disclosure.

In the examples of FIGS. 4A-4B, fasteners F1-F4 are formed as tubular structures that define channels that are sized to receive a segment of each of the fixation members 30a, 30b. In accordance with some examples, fasteners F1-F4 may be formed as discrete components, such as tubes, for example, that may be coupled to the capsule 34 through any suitable coupling techniques, which may include but are not limited to welding, bonding agents (e.g., a glue), frictional fitting, or crimping. Alternatively, in some examples, the fasteners may be formed integrally with the capsule 34. Fixation assembly 30 also may be coupled to fasteners F1-F4 by coupling techniques such as welding, bonding agents such as glue, frictional fitting, and crimping, although other coupling techniques may be used.

In some examples, the channels of fasteners F1-F4 may be defined to receive a segment of the fixation assembly 30 in a snug fit arrangement so as to prevent relative movement between capsule 34 and fixation assembly 30. By way of dimensional example, a thickness of a cross section of fixation assembly 30 may be on the order of approximately 0.15 millimeters (mm) for a round shape, or approximately 0.10 mm by 0.25 mm for a rectangular shape. In comparison, the diameter (or width) of the channel of each of the fasteners may be on the order of approximately 0.10 mm to 0.65 mm.

The free ends of fixation assembly 30 may be oriented in opposing directions. For example, a first of the free ends may be oriented downward in relation to first lateral sidewall SW1 and second lateral sidewall SW2, whereas a second of the free ends may be oriented upward in relation to first lateral sidewall SW1 and second lateral sidewall SW2, as shown in FIG. 4A. Such an orientation may be beneficial to the operation of sensor assembly 10, such as by imparting a degree of load cancellation that minimizes load transfer to sensing element 32.

In other examples, a first end of fixation member 30 may be coupled to a lateral sidewall, such as first lateral sidewall SW1, as shown in FIG. 4A, whereas a second end of fixation structure 30 may be coupled to a longitudinal wall, such as longitudinal wall LW1 or longitudinal wall LW2, as shown in FIG. 4B.

Figure 5:
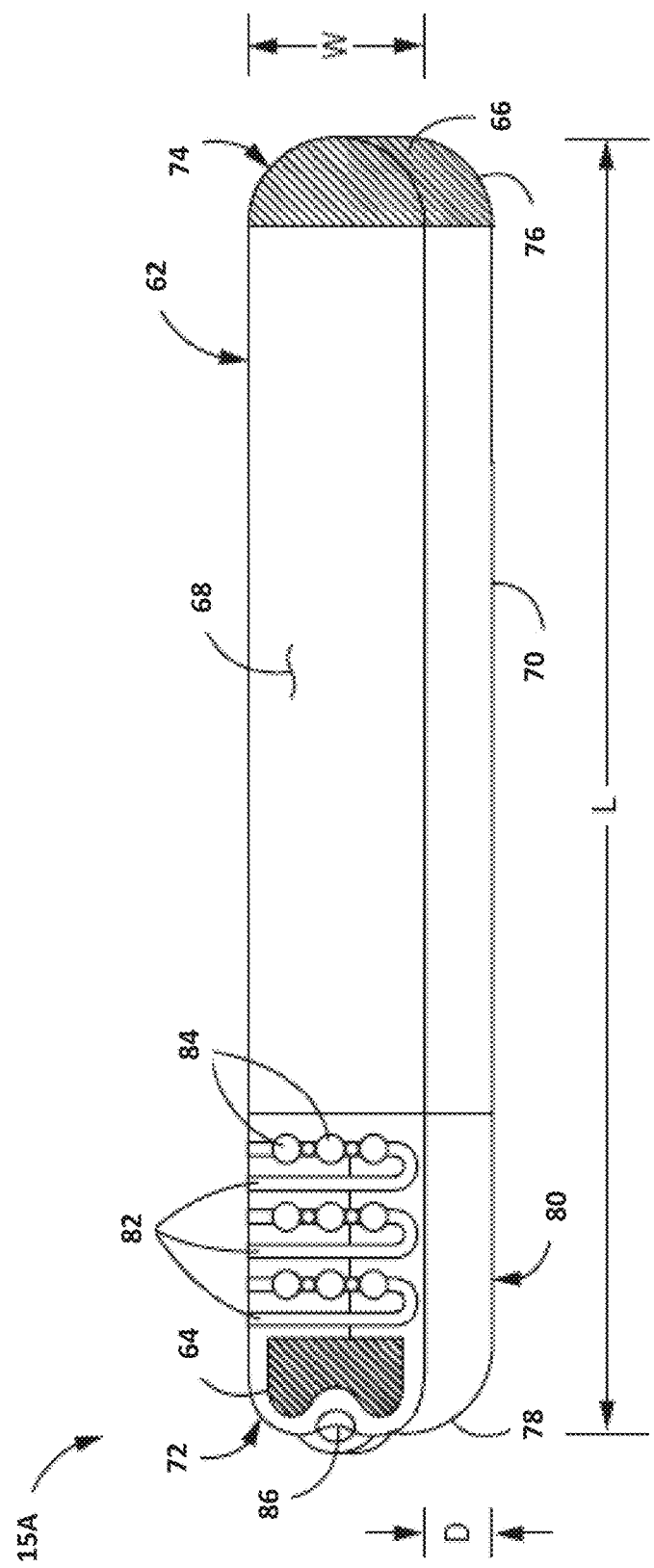
FIG. 5 is a conceptual drawing illustrating an example configuration of an insertable cardiac monitor.

FIG. 5 is a conceptual drawing illustrating an example configuration of ICM 15A of FIG. 1A. In the example shown in FIG. 5, ICM 15A may comprise a monitoring device having housing 62, proximal electrode 64, and distal electrode 66. Housing 62 may further comprise first major surface 68, second major surface 70, proximal end 72, and distal end 74. In some examples, housing 62 encloses electronic circuitry located inside the ICM 15A, and protects the circuitry contained therein from fluids such as body fluids. In the example depicted in FIG. 5, electrical feedthroughs provide electrical connection of electrodes 64 and 66 to circuitry within housing 62. In an example, the feedthrough described herein may be used with ICM 15A.

In the example shown in FIG. 5, ICM 15A is defined by a length L, a width W, and thickness or depth D. In this example, ICM 15A is in the form of an elongated rectangular prism wherein length L is significantly larger than width W, and wherein width W is larger than depth D. However, other configurations of ICM 15A are contemplated, such as those in which the relative proportions of length L, width W, and depth D vary from those described and shown in FIG. 5. In one example, the geometry of the ICM 15A—in particular, a width W greater than the depth D—is selected to allow ICM 15A to be inserted under the skin of the patient using a minimally invasive procedure and to remain in the desired orientation during insertion. For example, the device shown in FIG. 5 includes radial asymmetries (notably, the rectangular shape) along a longitudinal axis, which maintains the device in the proper orientation following insertion. For example, in one example the spacing between proximal electrode 64 and distal electrode 66 may range from about 30-55 mm, about 35-55 mm, or about 40-55 mm, and may be any range or individual spacing from about 25-60 mm. In addition, ICM 15A may have a length L that ranges from about 30-70 mm. In other examples, the length L may range from about 40-60 mm or about 45-60 mm, and may be any length or range of lengths between about 30-70 mm. In addition, the width W of major surface 68 may range from about 3-10 mm and may be any single or range of widths between about 3-10 mm. The thickness of depth D of ICM 15A may range from about 2-9 mm. In other examples, the depth D of ICM 15A may range from about 2-5 mm and may be any single or range of depths from about 2-9 mm. In addition, ICM 15A according to an example of the present disclosure is has a geometry and size designed for ease of implant and patient comfort. Examples of ICM 15A described in this disclosure may have a volume of 3 cubic centimeters ($cm^3$) or less, 1.5 $cm^3$ or less, or any volume therebetween. In addition, in the example shown in FIG. 5, proximal end 72 and distal end 74 are rounded to reduce discomfort and irritation to surrounding tissue once inserted under the skin of the patient. ICM 15A, including instrument and method for inserting ICM 15A is described, for example, in U.S. Patent Publication No. 2014/0276928, incorporated herein by reference in its entirety.

In the example shown in FIG. 5, the first major surface 68 of ICM 15A faces outward, i.e., towards the skin, once inserted within the patient, whereas the second major surface 70 is located opposite the first major surface 68. Consequently, the first and second major surfaces may face in directions along a sagittal axis of patient 2A (see FIG. 1A), and this orientation may be consistently maintained upon implantation due to the dimensions of ICM 15A. Additionally, an accelerometer, or axis of an accelerometer, may be oriented along the sagittal axis.

Proximal electrode 64 and distal electrode 66 are used to sense cardiac EGM signals, e.g., ECG signals, when ICM 15A is implanted in the patient either sub-muscularly or subcutaneously. Cardiac EGM signals may be stored in a memory of the ICM 15A, and data derived from the cardiac EGM signals may be transmitted via integrated antenna 82 to another medical device, which may be another implantable device or an external device, such as external device 14A. In some examples, electrodes 64 and 66 may additionally or alternatively be used for sensing any bio-potential signal of interest, e.g., an electroencephalogram (EEG), electromyogram (EMG), or a nerve signal, from any implanted location. Additionally, electrodes 64 and 66 may be used by communication circuitry, e.g., communication circuitry 168 (FIG. 6), for TCC communication with one or both of pressure sensing device 12A or external device 14A.

In the example shown in FIG. 5, proximal electrode 64 is in close proximity to proximal end 72, and distal electrode 66 is in close proximity to distal end 74. In this example, distal electrode 66 is not limited to a flattened, outward facing surface, but may extend from first major surface 68, around rounded edges 76 or end surface 78, and onto the second major surface 70. Thus, as shown in FIG. 5, electrode 66 may have a three-dimensional curved configuration. As illustrated, proximal electrode 64 is located on first major surface 68 and is substantially flat and outward facing. However, in other examples not shown here, proximal electrode 64 may incorporate the three-dimensional curved configuration of distal electrode 66, thereby providing a three-dimensional proximal electrode. Similarly, in other examples, distal electrode 66 may incorporate a substantially flat, outward facing electrode located on first major surface 68, similar to proximal electrode 64 as described above. The various electrode configurations described herein may allow for configurations in which proximal electrode 64 and distal electrode 66 are located on first major surface 68 and second major surface 70. In other configurations, such as that shown in FIG. 5, only one of proximal electrode 64 and distal electrode 66 is located on both major surfaces 68 and 70. In still other configurations, both proximal electrode 64 and distal electrode 66 are located on one of first major surface 68 or the second major surface 70 (i.e., with proximal electrode 64 located on first major surface 68 and distal electrode 66 located on second major surface 70). In another example, ICM 15A may include multiple electrodes on each of first major surface 68 and second major surface 70, such that a total of four electrodes are included on ICM 15A. In some examples, electrodes 64 and 66 may be formed of a biocompatible conductive material. For example, electrodes 64 and 66 may be formed from any of stainless steel, titanium, platinum, iridium, or alloys thereof. In addition, electrodes 64 and 66 may be coated with a material such as titanium nitride or fractal titanium nitride, although other suitable materials and coatings for electrodes 64 and 66 may be used.

In the example shown in FIG. 5, proximal end 72 includes header assembly 80 having one or more of proximal electrode 64, integrated antenna 82, anti-migration projections 84, and suture hole 86. Integrated antenna 82 is located on the same major surface (i.e., first major surface 68) as proximal electrode 64, and is provided as an integral part of header assembly 80, thereby allowing ICM 15A to transmit or receive data, e.g., via RF telemetry. In other examples, integrated antenna 82 may be formed on the major surface opposite from proximal electrode 64, or, in still other examples, may be incorporated within housing 62 of ICM 15A. In the example shown in FIG. 5, anti-migration projections 84 are located adjacent to integrated antenna 82 and protrude away from first major surface 68 so as to prevent longitudinal movement of ICM 15A. Anti-migration projections 84 may comprise a plurality of bumps or protrusions extending away from first major surface 68. As discussed above, in other examples anti-migration projections 84 may be located on the opposite major surface as proximal electrode 64 or integrated antenna 82. In addition, in the example shown in FIG. 5 header assembly 80 includes suture hole 86, which provides another means of securing ICM 15A to the patient to prevent movement following insertion. In the example shown, suture hole 86 is located adjacent to proximal electrode 64. In some examples, header assembly 80 may comprise a molded header assembly made from a polymeric or plastic material, and may be integrated or separable from the main portion of ICM 15A.

As described herein, some examples of the disclosure relate to implantable medical device and system that employ feedthroughs to provide an electrical connection between a battery or other electrochemical cell contained within an electrochemical cell compartment to electronics outside of the cell compartment.

In some examples, a feedthrough system (e.g., such as may include an electrically conducting pin and electrically conducting pad) may electrically couple two or more different sections of an IMD. For example, the feedthrough system may electrically couple electronics in an electronics compartment to an electrochemical cell (e.g., a battery) in an electrochemical cell compartment. In an example, the feedthrough system may electrically couple components such as electronics, capacitors, batteries, spaces inside or outside the electrochemical cell compartment, spaces inside or outside the IMD, or other components.

Figure 6:
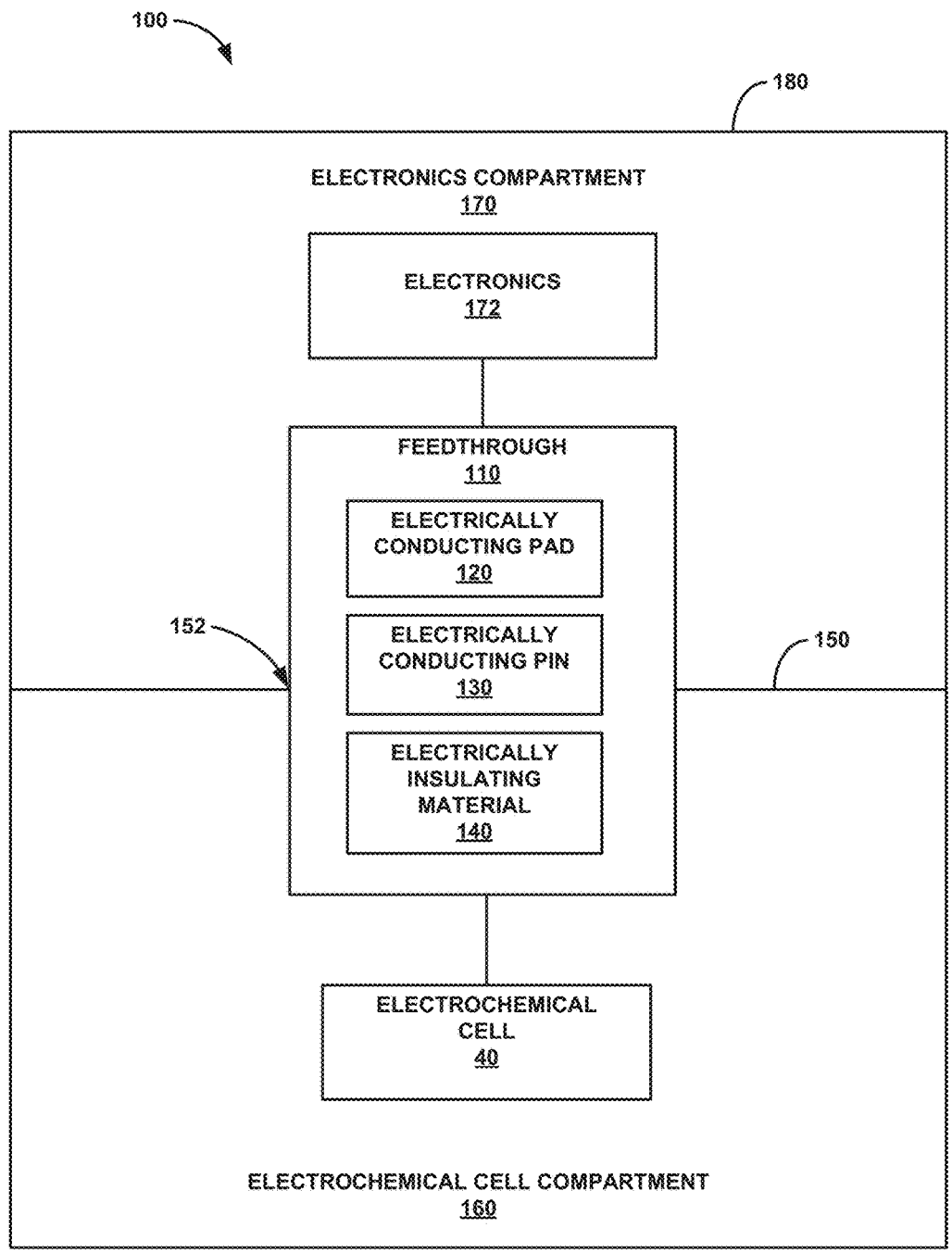
FIG. 6 is a schematic diagram illustrating an example system that includes a feedthrough.

FIG. 6 is a schematic diagram illustrating an IMD 100 in accordance with some examples of the disclosure. Examples of IMD 100 may include sensing devices 12A and 12B with capsule 34 described above. As shown, IMD 100 may include an outer housing 180. Outer housing 180 may be configured for placement into the body of the patient 2A, 2B (e.g., a biocompatible outer housing, and sized and shaped for implantation). This may include a rounded outer shape and hermetically sealed compartments. In some examples, IMD 100 may include fixation member coupled to the exterior of IMD 100, such as, e.g., those described with regard to capsule 34.

In some examples, electrochemical cell compartment 160 defines a barrier between the inside of electrochemical cell compartment 160 and the outside of electrochemical cell compartment 160. In some examples, electrochemical cell compartment 160 comprises cover portion 150, such as to aid in defining the barrier. Electrochemical cell 40 may be in the inside of electrochemical cell compartment 160. Electrically conducting pad 120 may include a top side and a bottom side. Electrically conducting pin 130 may be coupled to electrically conducting pad 120, such as may include extending from the bottom side of pad 120. Electrically conducting pad 120 may be positioned outside of electrochemical cell compartment 160, such as in electronics compartment 170. Electrically conducting pin 130 may extend through aperture 152. Aperture 152 may an opening defined by cover portion 150 in some examples. In other examples, aperture 152 may be an opening defined by the barrier defined by electrochemical cell compartment 160.

Pin 130 may extend through aperture 152 from inside electrochemical cell compartment 160 to pad 120 positioned outside of electrochemical cell compartment 160. This may allow for pin 130 to electrically couple electrochemical cell 40 to electrically conducting pad 120, such as to deliver power to electronics 172 in electronics compartment 170.

Electrically insulating material 140 may surround aperture 152. Electrically insulating material 140 may be between the bottom side of pad 120 and electrochemical cell compartment 160 (e.g., such as between pad 120 and cover portion 150, or between pad 120 and the barrier defined by compartment 160). Electrically insulating material 140 may be configured to insulate pad 120 from, for example, electrochemical cell compartment 160 or cover portion 150. Electrically insulating material 140 may form a seal between the inside of the electrochemical cell compartment 160 and the outside of the electrochemical cell compartment 160. The seal may be a hermetic seal. In some examples, the electrically insulating material is positioned within at least a portion of aperture 152 in the electrochemical cell compartment.

In other examples, the aperture is substantially vacant of the electrically insulating material. That is, electrically insulating material 140 may be dispensed or positioned between pad 120 and cover portion 150, and it may be possible for aperture 152 to be substantially vacant of electrically insulating material 140 even if a portion of electrically insulating material 140 spills over the edges of aperture 152, such as on a side of aperture 152 closer to electronics compartment 170. For example, aperture 152 may be substantially vacant of material 140 even if the material 140 is within about 0 percent to about 30 percent of a thickness of cover portion 150 (e.g., such as a percentage of T-CP of FIG. 10A). Electrically insulating material 140 may help to form a hermetic seal between the inside of electrochemical cell compartment 160 and the outside of electrochemical cell compartment 160.

In some examples, electrically insulating material 140 comprises a washer that may be positioned between pad 120 and compartment 160. The washer may include a washer aperture (e.g., washer aperture may be an opening defined by the washer). As such, pin 130 may extend through the washer aperture and then through aperture 152 to electrochemical cell 40, for example. In some examples, electrically insulating material 140 is configured to be thermally sealed.

In some examples, IMD 100 may include a first device section (e.g., such as electronics compartment 170), and a second device section (e.g., electrochemical cell compartment 160). In some examples, the outside of electrochemical cell compartment 160 includes the first device section. In some examples, the outside of electrochemical cell compartment 160 comprises one or more of an electronics compartment, an outside of IMD 100, or another compartment inside IMD 100. In some examples, the inside electrochemical cell compartment 160 comprises at least one of an electrochemical cell (e.g., cell 40), or a capacitor. In some examples, a feedthrough system may electrically couple one or more components located in the first and second device sections. Electrochemical cell compartment 160 may comprise a metal (e.g., titanium) housing.

In some examples, IMD 100 includes electronics compartment 170 and electrochemical cell compartment 160 within outer housing 180. Electronics compartment 170 may be a hermetically sealed compartment that encloses electronics 172. Electronics 172 may include electrical components and other devices that are supplied power from electrochemical cell 40 to operate as described. Example components may include processing circuitry, pressure sensor(s) or other sensors such as, e.g., MEMS and accelerometer sensors), telemetry components, switching circuitry, and the like, and may vary based on the desired function of device 100.

Similarly, electrochemical cell compartment 160 may be a hermetically sealed compartment within housing of IMD 100 that contains electrochemical cell 40. Electrochemical cell 40 may be in the form of a primary or secondary battery or other electrochemical cell that supplies operational power to electronic 173 via feedthrough 110. In some examples, cell 40 may include a solid-state battery. In an example, electrochemical cell 40 includes a lithium battery.

In some examples, electronics compartment 170, electrochemical cell compartment, electrically conducting pad 120, electrically conducting pin 130, and/or other components may comprise, consist, or consist essentially of a material such as aluminum, titanium, stainless steel (e.g., 304L stainless steel), or an alloy thereof.

In some examples, the IMD 100 may be configured with more than one housing (e.g., "double walled"). A first housing of the IMD 100 may be electrically insulated from a second housing of the electrochemical cell compartment 170 (e.g., the device wall may be electrically insulated from the battery wall). In an example, IMD 100 may include a hermetically sealed battery within another hermetically sealed device. In such an arrangement, the device may remain electrically insulated from the battery wall. Also, for a device with an electrically insulated outer wall, the electronics or proper functioning of the device may not be able to tolerate potential outgassing from a battery (e.g., if a non-hermetically sealed battery releases, for example, hydrogen during its function, the device (e.g., the pressure monitor) may be affected. The feedthrough described herein may be applicable to such a hermetically sealed device. In other examples, the feedthrough described herein may be applicable to a device where the outer device wall is also the wall for the battery.

In some examples, section 38 containing battery 40 of assembly 10A of may correspond to the electrochemical cell compartment 160. In some examples, electronics compartment 170 may correspond to a portion of the interior cavity of capsule 34 of assembly 10A where electronics 172 are housed.

In an example, electronics compartment 170 and electrochemical cell compartment 160 may be coupled, such as by using a laser welded joint. As shown in FIG. 6, a substrate such as cover portion 150 may be positioned between electrochemical cell compartment 160 and electronics compartment 170, such as, e.g., to create a first hermetically sealed compartment with the electrochemical cell compartment 160 or a second hermetically sealed compartment with the electronics compartment 170. Cover portion 150 may include an aperture 152 (e.g., an opening in cover portion 150 where feedthrough 110 may be positioned). Aperture 152 may extend through the thickness of cover portion 150 between compartments 170 and 160.

Feedthrough 110 extends through aperture 152 in cover portion between compartments 170 and 160, and may include an electrically conducting pad 120, an electrically conducting pin 130, and an electrically insulating material 140. As will be described below, in an example, electrically conducting pad 120 is coupled to electrically conducting pin 130. In an example, electrically insulating material 140 may be disposed on cover portion 150. In an example, a thickness of cover portion 150 may be substantially uniform.

Feedthrough 110 may be configured such that electrically conducting pin 130 extends through aperture 152, and such that electrically conducting pad 120 is positioned outside of electrochemical cell compartment 160. In an example, electrically conducting pad 120 is positioned within electronics compartment 170. In an example, electrically insulating material 140 is positioned between electrically conducting pad 120 and cover portion 150. In this position, electrically insulating material 140 separates electrically conducting pad 120 from cover portion 150. Electrically conducting pad 120 and electrically conducting pin 130 may be electrically insulated from cover portion 150.

In some examples, electrically insulating material 140 may be disposed within at least a portion of aperture 152 between pin 130 and the wall of aperture 152. When electrically insulating material 140 is disposed within at least a portion of aperture 152, electrically conducting pin 130 may be insulated from cover portion 150. That is, electrically insulating material 140 may be positioned within aperture 152 between electrically conducting pin 130 and a perimeter of the aperture 152 to electrically insulate electrically conducting pin 130 from cover portion 150. Because aperture 152 may be an opening between electrochemical cell compartment 160 and electronics compartment 170, in an example, electrically insulating material 140 may aid in creating the hermetically sealed compartment (e.g., the hermetically sealed electronics compartment, and the hermetically sealed electrochemical cell compartment).

In an example, feedthrough 110 may aid in creating the hermetically sealed compartment. By positioning the electrically insulating material 140 between the electrically conducting pad 120 and the cover portion 150, a smaller thickness may be achieved (e.g., the combined thickness of the cover portion 150, the electrically insulating material 140, and the electrically conducting pad 120).

In some examples, the feedthrough system includes the electrically insulating material 140 on both the cover portion 150 and within the aperture 152. In other examples, the feedthrough system includes the electrically insulating material 140 on the cover portion 150 but not within the aperture 152.

Figure 7:
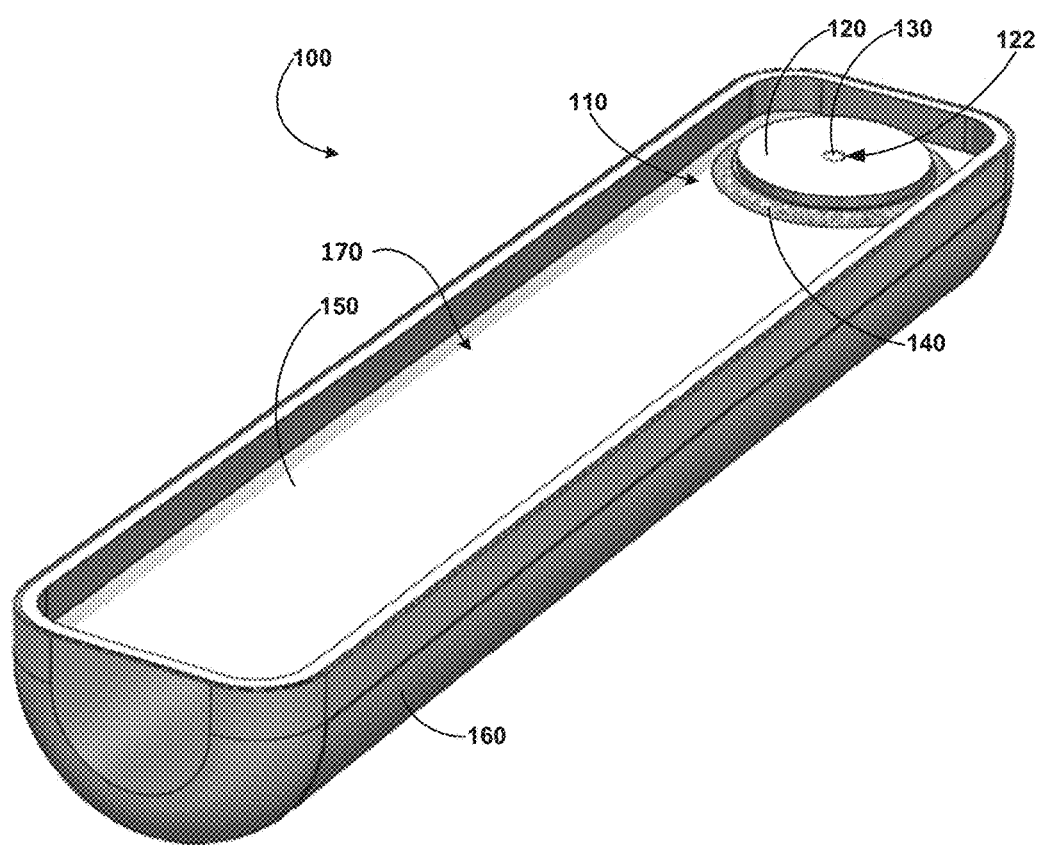
FIG. 7 illustrates an example of a view of portions of a medical device that includes a feedthrough.

FIG. 7 is a conceptual diagram illustrating an example of IMD 100 including feedthrough 110 in accordance with examples of the disclosure. As shown, IMD 100 includes electrochemical cell compartment 160 and electronics compartment 170. The top cover of electronics compartment 170 is not shown for purposes of illustration. As shown, conducting pad 120 and a portion of pin 130 are within electronics compartment 170, and an end portion of electrically conducting pin 130 is coupled to electrically conducting pad 120 within pad apertures 122.

Electrically conducting pad 120 may be sized and shaped to be housed within IMD 100 (e.g., entirely within electronics compartment 170. As shown further below with regard to FIG. 8, electrically conducting pin 130 may include first and second ends, such that one of the ends extends into pad aperture 122 to electrically couple pin 130 to pad 120, and the other of the ends of pin 130 extends through electrically insulating material 140 and through aperture 152 of cover portion 150. Electrically conducting pin 130 may be coupled to electrically conducting pad 120 such as, e.g., by using a laser welded joint. In another example, electrically conducting pad 120 and electrically conducting pin 130 may be manufactured as a single component, e.g., compared to multiple components later mechanically coupled to each other.

In an example, an electrochemical cell (e.g., a battery or a micro electrochemical cell) may be within electrochemical cell compartment 160 (e.g., a battery enclosure). Electrochemical cell compartment 160 may be defined by walls formed of a metal or a metal alloy, such as may include a titanium material. Electrically conducting pin 130 may be connected to a first polarity of electrochemical cell inside electrochemical cell compartment 160. IMD 100 may include electronics 172, such as in electronics compartment 170, and electronics 172 may be connected to the first polarity of the electrochemical cell via electrically conducting pad 120 and electrically conducting pin 130, such that the electrochemical cell supplies operating power to electronics 172.

In an example, the pin (e.g., electrically conducting pin 130) may coupled to the pad (e.g., electrically conducting pad 120), and the primary battery (e.g., electrochemical cell 40) coupling is from the pad to the case (e.g., housing 180). The pin itself may not necessarily be coupled directly to, for example, the seal (e.g., electrically insulating material 140), or other portions of the feedthrough assembly or IMD 100. In an example, electrically conducting pin 130 may comprise any conductive material that is metallurgically compatible with electrically conducting pad 120. Any such material robust to the battery electrolyte may be used. Electrically conducting pin 130 may be configured to be used with the battery electrolyte of the electrochemical cell 40. In some examples, electrically conducting pin 130, electrically conducting pad 120, and other portions of IMD 100 may comprise titanium, titanium alloys, or other materials, such as may include nickel. Electrically conducting pad 120 and electrically conducting pin 130 may be formed of a conductive material, such as tantalum (Ta), niobium (Nb), titanium (Ti), platinum (Pt), iridium (Ir) or alloys thereof. In an example, electrically conducting pad 120 may comprise a titanium conductor with a nobelized surface, such as for a pressure contact interconnect. In one example, any conductor may be used for the pin or the pad, provided a wetting on the conductor is possible, such as may be compatible with glass or other thermally activated materials (e.g., a polymer). In an example, for some battery chemistries, electrically conducting pad 120 may comprise a material including niobium, and electrically conducting pin 130 may comprise nickel, such as may be used for hermetic sealing with the glass material for electrically insulating material 140. In other examples, electrically insulating material 140 may comprise other thermally active materials, such as a polymer. In some examples, electrically conducting pad 120 and electrically conducting pin 130 may be machined, stamped, or otherwise manufactured from a single piece. In other examples, the pin may be laser welded or restrictive welded to other components, such as the pad. In an example, IMD 100 may include a solid-state battery, and feedthrough 110 may be advantageous for such use.

As shown in FIG. 7, insulating material 140 is disposed on the top surface of cover portion 150 and is between the top surface of cover portion 150 and conducting pad 120. In such a configuration, insulating material 140 mechanically couples conducting pad 120 to cover portion 150 and also electrically insulates cover portion 150 from conducting pad 120. In an example, electrically insulating material 140 may comprise a reflowed glass frit material. As will be described below, the glass frit may be deposited as a paste, e.g., via screen printing or a syringe, and then undergo thermal processing to bond conducting pad 120 to cover portion 150.

Glass for electrically insulating material 140 may comprise boro-alumino, boro-alumino silicate, or boro silicate type glasses with a wide range of thermal expansions to approximately match electrically conducting pad 120 materials such as Ta, Nb, niobium-titanium (Nb—Ti) alloy, Pt, Pt alloys, Ti, alloys of Ti, or other suitable materials. In an example, two primary properties of the glass seal (such as electrically insulating material 140) may include a thermal expansion coefficient that may be mechanically compatible with sealing the pad (e.g., electrically conducting pad 130) to the case (e.g., cover portion 150), and corrosion resistance to the battery electrolyte (e.g., lithium) system. In an example, borate glasses may be used for such a glass seal. The seal or electrically insulating material 140 may include other examples, such as described by U.S. Pat. No. 8,129, 622 to Taylor et al., entitled, "INSULATOR FOR FEEDTHROUGH," which issued on Mar. 6, 2012, incorporated herein by reference in its entirety.

Figure 8:
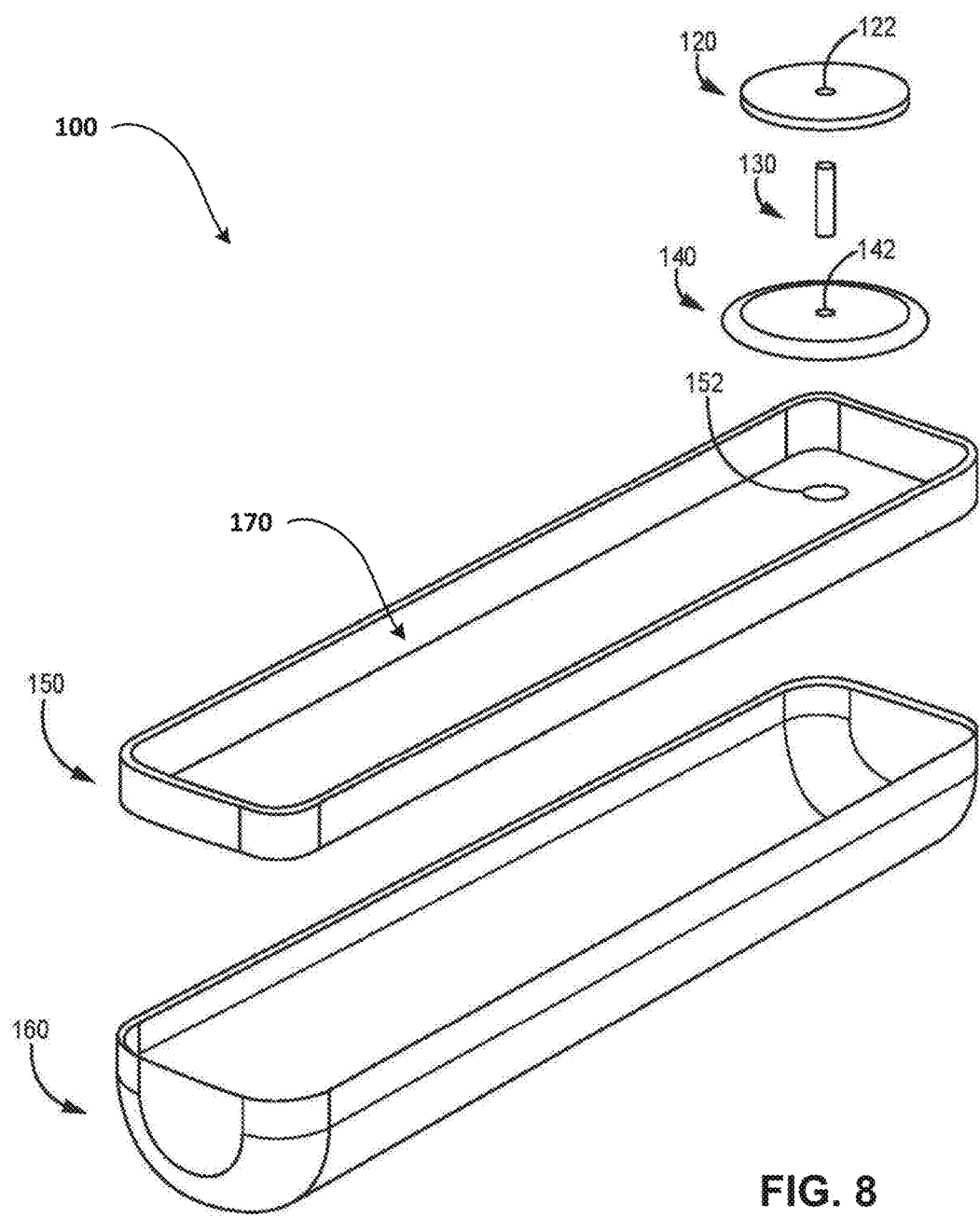
FIG. 8 is an exploded perspective view of an example of a system that includes a feedthrough.

FIG. 8 is an exploded perspective view of IMD 100 of FIG. 7. This exploded perspective view shows a relative arrangement of portions of IMD 100. For example, electrically conducting pin 130 may be seen as configurable within pad aperture 122. Electrically conducting pin 130 may extend through an insulating aperture 142 of electrically insulating material 140 (such as when electrically insulating material 140 is formed into a washer shape). In an example, the electrically insulating material 140 may be dispensed as a paste, or may be "dropped in" or placed as a preformed piece. In an example, insulating aperture 142 is aligned with aperture 152 of cover portion 150. Electrochemical cell compartment 160 and electronics compartment 170 may be machined or draw formed compartments, and may be formed of a metal (e.g., titanium) or metal alloy material. In an example, cover portion 150 may be a machined or stamped metal cover, and may be formed of the metal or metal alloy. In an example, electrically insulating material 140 is a glass frit material (e.g., a low temperature reflow). In an example, feedthrough 110 is an electrical feedthrough including an interconnection pad (e.g., electrically conducting pad 120) that minimally uses the internal volume of IMD 100.

In an example, electrically insulating material 140 may comprise a mix of thin glass pieces and paste, such as where a preformed washer includes a glass piece and the aperture of the washer may be filled with paste, or vice versa.

Figure 9A:
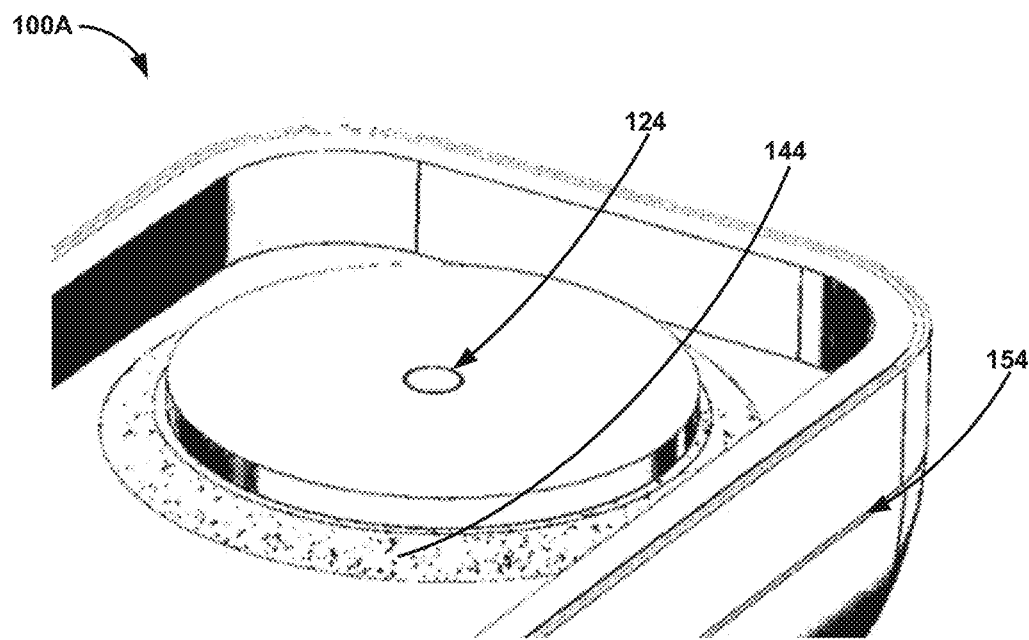
FIG. 9A illustrates an example of portions of a system that includes a feedthrough.
Figure 9B:
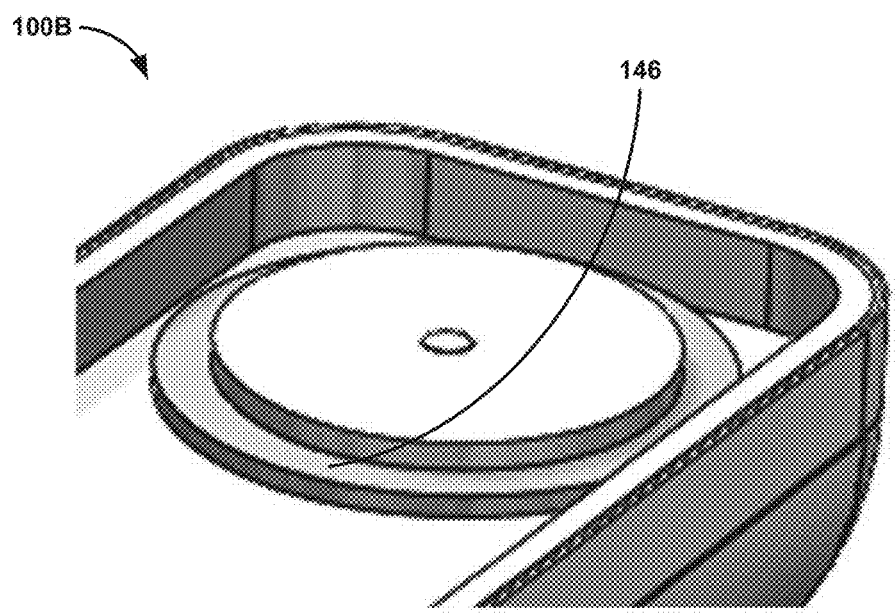
FIG. 9B illustrates an example of portions of a system that includes a feedthrough.

FIG. 9A illustrates an example IMD 100A similar to that of IMD 100 that includes electrically insulating material 144 that comprises a frit (e.g., the reflowed glass frit material, or the low temperature reflow). FIG. 9B illustrates another example of IMD 100B similar to that of IMD 100 that includes a feedthrough in which electrically insulating material 146 that comprises a thermoplastic (e.g., a thermoplastic seal, or an acid modified polypropylene or "PPaF"). In an example, electrically insulating material 144 may comprise glass or an acid modified polypropylene. Electrically conducting pin 130 may comprise titanium, such as may be used for chemical compatibility with electrochemical cell 40, and may provide ease of use for laser welding to electrically conducting pad 120.

Referring to FIG. 9A, first joint 124 may join electrically conducting pad 120 and electrically conducting pin 130. A second joint 154 may join electrochemical cell compartment 160 and cover portion 150. The first and second joints 124, 154 may be a laser welded joint, a spot weld (e.g., a resistance spot weld or an "electric resistance weld"), an interference fit (also referred to as mechanical interference or a "friction fit"), or other joining techniques. Other components of the IMDs 100, 100A, 100B may similarly be joined, such as cover portion 150 and electronics compartment 170. Electronics within the electronics compartment, for example, may be joined to electrically conducting pad 120.

Figure 10A:
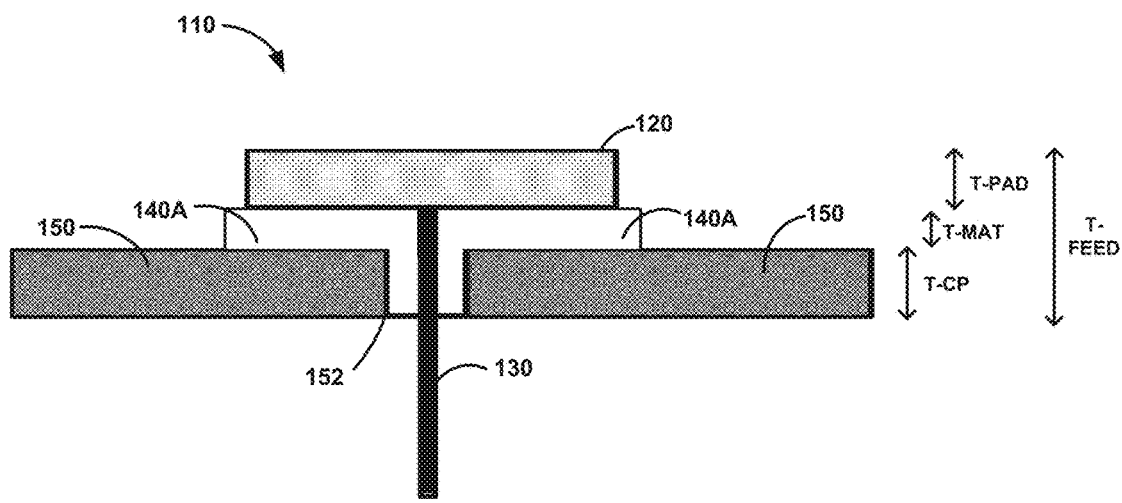
FIGS. 10A and 10B are conceptual diagrams illustrating cross-sections of an example of a feedthrough.
Figure 10B:
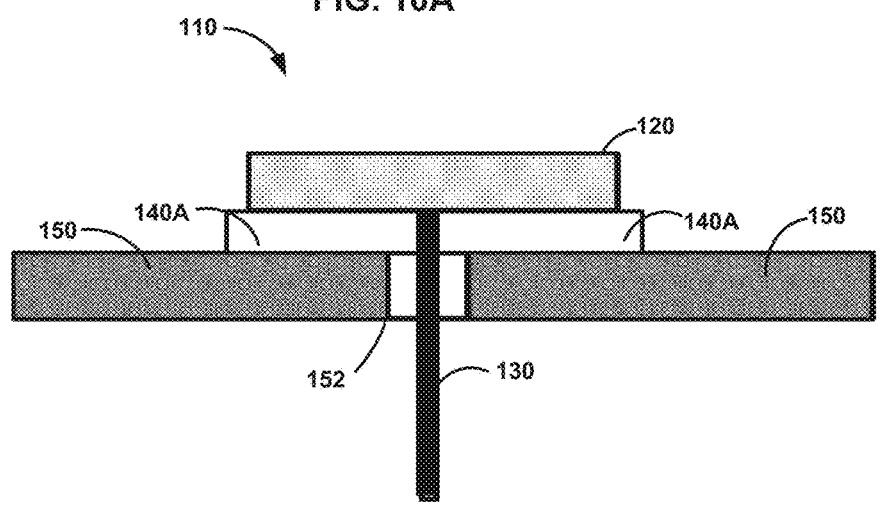

FIGS. 10A and 10B are conceptual drawing illustrating a cross-sectional view of feedthrough 110 extending through aperture 152 in cover portion 152. In an example, feedthrough 110 includes electrically insulating material 140A. In FIG. 10A, electrically insulating material 140A may be seen as both separating electrically conducting pad 120 and cover portion 150, and positioned within a perimeter of aperture 152 of cover portion 150 and electrically insulating electrically conducting pin 130 from the cover portion. That is, electrically insulting material 140A may include an aperture seal portion positioned within aperture 152 and surrounding electrically conducting pin 130. In some examples, electrically insulating material 140A may extend only partially through aperture 152. As shown in FIG. 10B, in another example, electrically insulting material 140A does not extend into aperture 152 but is positioned between the top surface of cover portion 150 and opposing surface of conducting pad 120. In an example, feedthrough 110 includes electrically insulating material 140A, and thereby is configured to form a hermetic seal between electrochemical cell compartment 160 and electronics compartment 170.

As described herein, the configuration of feedthrough 110 and IMD 100 may allow for feedthrough to exhibit a relatively low profile. Referring to FIG. 10A, the thickness of cover portion 150 ("T-CP") may be about 0.005 inches to about 0.015 inches, such as, e.g., about 0.008 inches to about 0.010 inches. In some examples, T-CP is substantially uniform. The thickness of electrically insulating material 140A ("T-MAT") may be about 0.003 inches to about 0.010 inches, such as, e.g., about 0.004 inches to about 0.006 inches. In one example, T-CP may be about 0.005 inches to about 0.008 inches. The thickness of electrically conducting pad 120 ("T-PAD") may be about 0.003 inches to about 0.008 inches, such as, e.g., about 0.004 inches to about 0.005 inches. In one example, T-PAD may be about 0.005 inches to about 0.015 inches. A combined thickness of the cover portion, the electrically insulating material, and the electrically conducting pad (e.g., a feedthrough thickness or "T-FEED") may be about 0.015 inches to about 0.020 inches, such as, e.g., about 0.016 inches to about 0.017 inches.

In some examples, T-FEED may be about 0.010 inches to about 0.035 inches, such as, e.g., about 0.011 inches to about 0.033 inches. Other dimensions for the various parameters listed above are contemplated.

Although the bottom end of pin 130 is shown in FIGS. 10A and 10B as extending out of the bottom surface of cover portion 150 for some length, it is noted that pin 130 may end at approximately the same plane as that of the bottom surface of cover portion 150, e.g., by trimming pin 130 once pin 130 has been located within aperture 152. As noted above, the bottom end portion of pin 130 may be electrically and mechanically coupled to a polarity of electrochemical cell 40 within cell compartment 160.

Figure 10C:
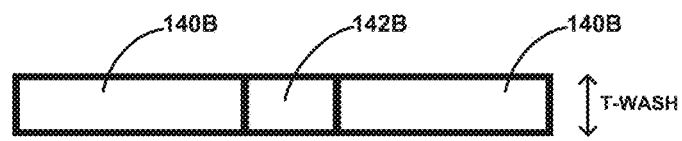
FIG. 10C is a conceptual drawing illustrating an example preformed insulating portion of a feedthrough.

FIG. 10C is a conceptual drawing illustrating another example of electrically insulating material 140B that may be utilized with feedthrough 100. Unlike that of a glass frit formed from a paste, electrically insulating material 140B may take the form of a preformed washer that may include a washer aperture 142B. In some examples, the washer may be in the form of a ceramic such as glass. A thickness of electrically insulating material 140B in the washer shape ("T-WASH") may be about 0.003 inches to about 0.010 inches, such as, e.g., about 0.004 inches to about 0.006 inches.

A potential advantage of the present subject matter may include that the feedthrough does not require a ferrule. In an example, this may reduce the cost and complexity of manufacturing the feedthrough. In an example, by not using a ferrule, the relative volume of the battery within the device may be larger as the insulating seal may be positioned outside of the electrochemical cell compartment 160. In an example, this arrangement puts the volume consumption of the seal in "free space" (e.g., outside the battery) rather than consuming internal battery volume, such as may allow for optimization of active battery material.

A potential advantage of the present subject matter may include that the feedthrough disclosed in this document may be used with devices that include small batteries, such as for relatively smaller implantable devices. For example, the relative amount of space that the feedthrough takes up in the device may be decreased. A very compact battery may be at least partially achieved by a low-profile feedthrough, such as described herein. For example, the feedthrough uses a relatively smaller percentage of volume of IMD 100. In an example, for case wall thicknesses that may be used with IMD 100 and other overhead, the smaller the volume of IMD 100, the more that packaging overhead matters, such as from a percentage of volume impact. For example, a feedthrough assembly that comprises 0.1 cc used with a 10 cc battery presents less of a challenge than a feedthrough assembly that comprises 0.1 cc used with a 0.3 cc battery. In an example, the present matter may be advantageous to address such challenges.

Any suitable technique may be employed to form the feedthroughs and medical devices described herein. Example techniques include those examples described below. For ease of description, the example techniques are described with regard to IMD 100 described above.

Figure 11:
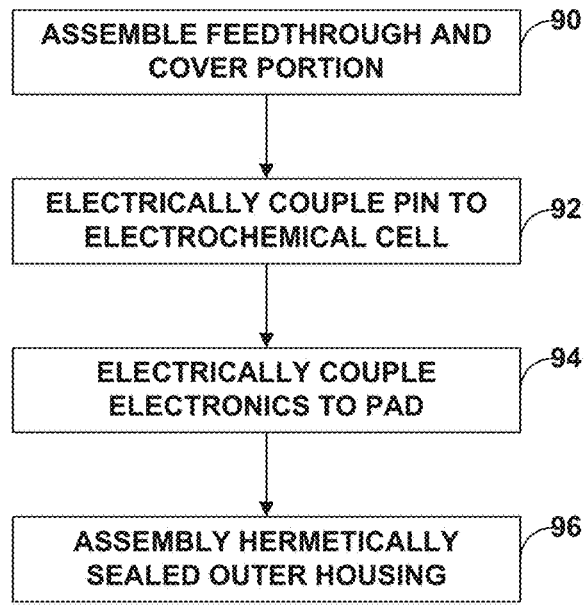
FIG. 11 is a flow diagram illustrating an example technique in accordance with the disclosure.

FIG. 11 is a flow diagram illustrating one example technique for fabricating IMD 100. As shown, feedthrough 110 may be assembled with cover portion 150, e.g., in the configurations shown in FIG. 7-9B, to form a hermetic seal between conducting pad 120/pin 130 and cover portion 150 (90). Pin 130 of feedthrough 110 may then be electrically coupled to electrochemical cell 40 within electrochemical cell compartment 160, and cover portion 150 may be positioned over the complementary bottom portion of the outer housing to form cell compartment 160 (92). Conductive pad 120 may be electrically coupled to electronics 172 within electronic compartment 170 such that electronics 172 are electrically coupled to electrochemical cell 40 via feedthrough 110 so that electrochemical cell 40 may supply operational power to electronics 170 (94). Outer housing 180 of IMD 100 may then be assembly to seal electronics 172 and electrochemical cell within housing 180 (96).

Figure 12:
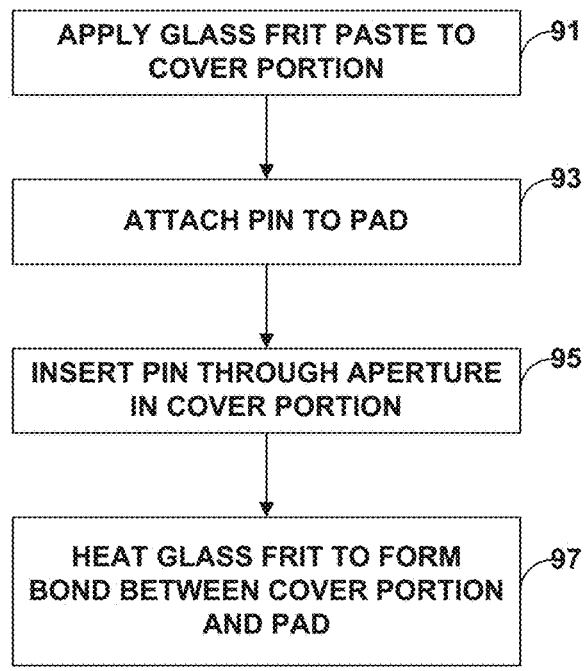
FIG. 12 is a flow diagram illustrating an example technique in accordance with the disclosure.

FIG. 12 is a flow diagram illustrating one example technique for assembling feedthrough 110 with conducting pin 130 extending through aperture 152 with conducting pad 120 separated from the opposing surface of cover portion 150 by insulating material 140. For example, as shown in FIG. 12, glass frit paste or other insulating material may be disposed around or in aperture 152 as desired, e.g., using a screen printing, syringe dispensing or other suitable technique (91). An end portion of conducting pin 130 may be attached to conducting pad 120 (e.g., by laser welding the end of pin 130 within pin aperture 122 in conducting pad 120 (93). In other examples, pin 130 and pad 120 may be initially constructed as a single component. Conducting pin 130 may then be positioned through aperture 152 in cover portion 150 with the bottom surface of conducting pad 120 in contact with the previously deposited glass frit paste (95). The assembly of the conducting pad 120, conducting pin 130, cover portion 150 and glass frit paste 140 may undergo one or more thermal processing steps (e.g., within a furnace) to raise the temperature of the glass frit paste 140 to bond conducting pad 120 to the opposing surface of cover portion 150 and form a hermetic seal (97). In cases which paste 140 extends within at least a portion of aperture 152, pin 130 may be bonded to the opposing walls of aperture 152

In examples in which paste 140 does not extend into aperture 152, paste 140 may be heated via direct energy (e.g., a laser) to form the bond between conducting pad 120 and the opposing surface of cover portion 150 rather than or in addition to heating within a furnace.

Similar techniques may be used to form a bond between conducting pad 120 and the opposing surface of cover portion 150 in cases in which electrically insulating material 140 takes the form of a thermal setting polymer rather than a glass frit.

In examples in which electrically insulating material 140 includes a preform material (e.g., a glass washer), the preform may be positioned to surround aperture 152

In some examples, electrically insulating material 140 may be underfilled between conducting pad 120 and cover portion 150 after pin 130 and pad 120 have been positioned as desired in addition to or as an alternative to depositing electrically insulating material 140 prior to positioning of conductive pad 120 and pin 130.

The above techniques are exemplary. Any suitable techniques may be used to fabricate the structures described herein and may vary based on the particular materials employed for the respective components.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided.

Example 1 may include subject matter (such as a system, a method, a means for performing acts) that may include an implantable medical device. The implantable medical device may include an outer housing; an electrochemical cell compartment within the outer housing; an electronics compartment within the outer housing; a cover portion positioned between the electrochemical cell compartment and the electronics compartment within the outer housing, the cover portion may include an aperture extending between the electrochemical cell compartment and the electronics compartment; a feedthrough that may include an electrically conducting pad coupled to an electrically conducting pin, the electrically conducting pin extending through the aperture, the electrically conducting pad may be positioned outside of the electrochemical cell compartment and within the electronics compartment within the outer housing; and an electrically insulating material that may be disposed on the cover portion and within at least a portion of the aperture, the electrically insulating material may be positioned between the electrically conducting pad and the cover portion, the electrically insulating material positioned within the aperture between the electrically conducting pin and a perimeter of the aperture to electrically insulate the electrically conducting pin from the cover portion, and the electrically insulating material configured to separate the electrically conducting pad and the cover portion.

In Example 2, the subject matter of Example 1 may optionally be configured such that the electrically insulating material may include an aperture seal portion positioned within the aperture and surrounding the electrically conducting pin.

In Example 3, the subject matter of any one or any combination of Examples 1-2 may optionally be configured such that the electrically conducting pad is coupled to the electrically conducting pin by a laser welded joint.

In Example 4, the subject matter of any one or any combination of Examples 1-3 may optionally be configured such that the outer housing and the cover portion are mechanically coupled by a laser welded joint.

In Example 5, the subject matter of any one or any combination of Examples 1-4 may optionally be configured such that the feedthrough includes the electrically insulating material, and wherein the feedthrough forms a hermetic seal between the electrochemical cell compartment and an electronics compartment.

In Example 6, the subject matter of any one or any combination of Examples 1-5 may optionally be configured such that the electrically insulating material comprises a frit.

In Example 7, the subject matter of any one or any combination of Examples 1-6 may optionally be configured such that the frit comprises a reflowed glass frit material.

In Example 8, the subject matter of any one or any combination of Examples 1-7 may optionally be configured such that the frit comprises low temperature reflow.

In Example 9, the subject matter of any one or any combination of Examples 1-8 may optionally be configured such that the electrically insulating material comprises a plastic.

In Example 10, the subject matter of any one or any combination of Examples 1-9 may optionally be configured such that the plastic comprises a thermoplastic seal.

In Example 11, the subject matter of any one or any combination of Examples 1-10 may optionally be configured such that the plastic comprises an acid modified polypropylene.

In Example 12, the subject matter of any one or any combination of Examples 1-11 may optionally be configured such that the cover portion comprises a metal cover portion.

In Example 13, the subject matter of any one or any combination of Examples 1-12 may optionally be configured such that the metal cover portion comprises a titanium metal cover portion.

In Example 14, the subject matter of any one or any combination of Examples 1-13 may optionally be configured such that the housing comprises a metal housing.

In Example 15, the subject matter of any one or any combination of Examples 1-14 may optionally be configured such that the electrochemical cell compartment is a titanium battery enclosure.

In Example 16, the subject matter of any one or any combination of Examples 1-15 may optionally be configured such that a thickness of the cover portion is about 0.005 inches to about 0.015 inches.

In Example 17, the subject matter of any one or any combination of Examples 1-16 may optionally be configured such that the electrically insulating material includes an insulating layer, and wherein a thickness of the insulating layer between the cover portion and electrically conducting pad is about 0.003 inches to about 0.010 inches.

In Example 18, the subject matter of any one or any combination of Examples 1-17 may optionally be configured such that the electrically insulating material includes an insulating layer, and wherein a thickness of the cover portion, the insulating layer, and the electrically conducting pad combined is about 0.015 inches to about 0.020 inches.

In Example 19, the subject matter of any one or any combination of Examples 1-18 may optionally be configured such that a thickness of the cover portion is substantially uniform.

In Example 20, the subject matter of any one or any combination of Examples 1-19 may optionally be configured such that the implantable medical device may comprise an electrochemical cell within the electrochemical cell compartment, wherein the electrically conducting pin is connected to a first polarity of the electrochemical cell inside the electrochemical cell compartment.

In Example 21, the subject matter of any one or any combination of Examples 1-20 may optionally be configured such that the implantable medical device may comprise electronics in the electronics compartment connected to first polarity of the electrochemical cell via the pad and the pin such that the electrochemical cell supplies operating power to the electronics.

Example 22 may include, or may be combined with the subject matter of one or any combination of Examples 1-21 to optionally include, subject matter (such as an apparatus, a method, or a means for performing acts) that may include a method for manufacturing an implantable medical device including an outer housing, an electrochemical cell compartment within the outer housing, and an electronics compartment within the outer housing. The method may comprise positioning a feedthrough including an electrically conducting pad coupled to an electrically conducting pin such that the electrically conducting pin extends through an aperture in a cover portion, wherein the cover portion is configured to be positioned between the electrochemical cell compartment and the electronics compartment within the outer housing and wherein positioning the feedthrough includes positioning the electrically conducting pad outside of the electrochemical cell compartment and within the electronics compartment within the housing. The method may comprise disposing an electrically insulating material on the cover portion and within at least a portion of the aperture, the electrically insulating material positioned within the aperture between the electrically conducting pin and a perimeter of the aperture to electrically insulate the electrically conducting pin from the cover portion, and the electrically insulating material separating the electrically conducting pad and the cover portion.

In Example 23, the subject matter of any one or any combination of Examples 1-22 may optionally be configured such that disposing the electrically insulating material on the cover portion includes dispensing a frit onto at least one of an upper portion of the cover portion, and within the aperture; and wherein positioning the electrically conducting pin to extend through the aperture includes positioning the electrically conducting pin to extend through the frit.

In Example 24, the subject matter of any one or any combination of Examples 1-23 may optionally be configured such that disposing the electrically insulating material on the cover portion occurs after positioning the feedthrough.

In Example 25, the subject matter of any one or any combination of Examples 1-24 may optionally be configured such that disposing the electrically insulating material on the cover portion includes positioning a washer on the cover portion, wherein the electrically insulating material includes the washer.

In Example 26, the subject matter of any one or any combination of Examples 1-25 may optionally be configured such that filling an opening of the washer with additional electrically insulating material.

In Example 27, the subject matter of any one or any combination of Examples 1-26 may optionally be configured such that disposing the electrically insulating material on the cover portion includes thermally sealing the electrically insulating material by providing energy to the electrically insulating material.

Example 28 may include, or may be combined with the subject matter of one or any combination of Examples 1-27 to optionally include, subject matter (such as an apparatus, a method, or a means for performing acts) that may include a feedthrough that may include an electrically conducting pad coupled to an electrically conducting pin, the electrically conducting pin; and wherein the feedthrough may include an electrically insulating material disposed on a first side of the electrically conducting pad and around at least a portion of the electrically conducting pin, the electrically insulating material may be configured to be positioned between the electrically conducting pad and a cover portion, the electrically insulating material may be configured to be positioned within an aperture of the cover portion between the electrically conducting pin and a perimeter of the aperture to electrically insulate the electrically conducting pin from the cover portion, and the electrically insulating material may be configured to separate the electrically conducting pad and the cover portion.

In Example 29, the subject matter of any one or any combination of Examples 1-28 may optionally be configured such that the cover portion may be part of an outer housing, wherein an electrochemical cell is within the outer housing, and wherein the electrically conducting pin may extent through the aperture and into electrochemical cell.

Example 30 may include, or may be combined with the subject matter of one or any combination of Examples 1-27 to optionally include, subject matter (such as an apparatus, a method, or a means for performing acts) that may include an implantable medical device (IMD) that may comprise an electrochemical cell compartment that may define a barrier between an inside of the electrochemical cell compartment and an outside of the electrochemical cell compartment. The IMD may comprise an electrically conducting pad. The IMD may comprise an electrically conducting pin that may be coupled to the conducting pad, wherein the electrically conducting pad includes a top side and a bottom side, wherein the electrically conducting pin may extend from the bottom side of the conducting pad, wherein the electrically conducting pad may be positioned outside of the electrochemical cell compartment and the electrically conducting pin may extend through an aperture in the compartment from inside the electrochemical cell compartment to the electrically conducting pad positioned outside of the electrochemical cell compartment. The IMD may comprise an electrically insulating material that may surround the aperture and between the bottom side of the electrically insulating pad and the electrochemical cell compartment, and wherein the electrically insulating material may be configured to insulate the electrically conducting pad from the barrier and form a seal between the inside of the electrochemical cell compartment and the outside of the electrochemical cell compartment.

In Example 31, the subject matter of any one or any combination of Examples 1-30 may optionally be configured such that the seal may comprise a hermetic seal between the inside of the electrochemical cell compartment and the outside of the electrochemical cell compartment.

In Example 32, the subject matter of any one or any combination of Examples 1-31 may optionally be configured such that the electrically insulating material may be positioned within at least a portion of the aperture in the electrochemical cell compartment.

In Example 33, the subject matter of any one or any combination of Examples 1-32 may optionally be configured such that the aperture may be substantially vacant of the electrically insulating material.

In Example 34, the subject matter of any one or any combination of Examples 1-33 may optionally be configured such that the electrically insulating material may comprise a washer positioned between the electrically conducting pad and the electrochemical cell compartment, wherein the washer includes a washer aperture, and wherein the electrically conducting pin extends through the washer aperture and through the aperture in the electrochemical cell compartment.

In Example 35, the subject matter of any one or any combination of Examples 1-34 may optionally be configured such that the electrically insulating material is configured to be thermally sealed.

In Example 36, the subject matter of any one or any combination of Examples 1-35 may optionally be configured such that the electrically conducting pad is coupled to the electrically conducting pin by a laser welded joint.

In Example 37, the subject matter of any one or any combination of Examples 1-36 may optionally be configured such that the outside of the electrochemical cell compartment comprises one of an electronics compartment, outside of the implantable medical device, or a compartment inside the implantable medical device.

In Example 38, the subject matter of any one or any combination of Examples 1-37 may optionally be configured such that the electrochemical cell compartment houses at least one of an electrochemical cell, or a capacitor.

In Example 39, the subject matter of any one or any combination of Examples 1-38 may optionally be configured such that the electrically insulating material comprises a frit.

In Example 40, the subject matter of any one or any combination of Examples 1-29 may optionally be configured such that the frit comprises a reflowed glass frit material.

In Example 41, the subject matter of any one or any combination of Examples 1-40 may optionally be configured such that the frit comprises low temperature reflow.

In Example 42, the subject matter of any one or any combination of Examples 1-41 may optionally be configured such that the electrically insulating material comprises a plastic.

In Example 43, the subject matter of any one or any combination of Examples 1-42 may optionally be configured such that the plastic comprises a thermoplastic seal.

In Example 44, the subject matter of any one or any combination of Examples 1-43 may optionally be configured such that the plastic comprises an acid modified polypropylene.

In Example 45, the subject matter of any one or any combination of Examples 1-44 may optionally be configured such that the electrically insulating material comprises an epoxy.

In Example 46, the subject matter of any one or any combination of Examples 1-45 may optionally be configured such that the electrochemical cell compartment comprises a metal housing.

In Example 47, the subject matter of any one or any combination of Examples 1-46 may optionally be configured such that the metal housing comprises a titanium metal housing.

In Example 48, the subject matter of any one or any combination of Examples 1-47 may optionally be configured such that the electrochemical cell compartment comprises a titanium battery enclosure.

In Example 49, the subject matter of any one or any combination of Examples 1-48 may optionally be configured such that a wall thickness of the electrochemical cell compartment is about 0.005 inches to about 0.015 inches.

In Example 50, the subject matter of any one or any combination of Examples 1-49 may optionally be configured such that a wall thickness of the electrochemical cell compartment is substantially uniform.

In Example 51, the subject matter of any one or any combination of Examples 1-50 may optionally be configured such that a thickness of the electrically conducting pad between the top and bottom surface is about 0.003 inches to about 0.008 inches.

In Example 52, the subject matter of any one or any combination of Examples 1-51 may optionally be configured such that the electrically insulating material includes an insulating layer, and wherein a thickness of the insulating layer between the electrically conducting pad and the barrier is about 0.003 inches to about 0.010 inches.

In Example 53, the subject matter of any one or any combination of Examples 1-52 may optionally be configured such that the electrically insulating material includes an insulating layer, and wherein a thickness of the cover portion, the insulating layer, and the electrically conducting pad combined is about 0.015 inches to about 0.020 inches.

In Example 54, the subject matter of any one or any combination of Examples 53 may optionally be configured such that an electrochemical cell may be within the electrochemical cell compartment, wherein the electrically conducting pin is connected to a first polarity of the electrochemical cell inside the electrochemical cell compartment.

In Example 55, the subject matter of any one or any combination of Examples 1-54 may optionally be configured such that the IMD further comprises electronics outside electrochemical cell compartment, the electronics connected to the first polarity of the electrochemical cell via the electrically conducting pad and the electrically conducting pin such that the electrochemical cell supplies operating power to the electronics.

Example 56 may include, or may be combined with the subject matter of one or any combination of Examples 1-55 to optionally include, subject matter (such as an apparatus, a method, or a means for performing acts) that may include a method for manufacturing an implantable medical device (IMD). The IMD may include an electrochemical cell compartment that may define a barrier between an inside of the electrochemical cell compartment and an outside of the electrochemical cell compartment. The method may comprise positioning an electrically conducting pin to extend through an aperture in the electrochemical cell compartment, wherein the electrically conducting pin may be coupled to an electrically conducting pad including a top side and a bottom side, wherein the electrically conducting pad may be positioned outside of the electrochemical cell compartment. The method may comprise disposing an electrically insulating material surrounding the aperture and between the bottom side of the electrically conducting pad and the electrochemical cell compartment. The electrically insulating material may be configured to insulate the electrically conducting pad from the barrier and may form a seal between the inside of the electrochemical cell compartment and the outside of the electrochemical cell compartment.

In Example 57, the subject matter of any one or any combination of Examples 1-56 may optionally be configured such the method may include disposing the electrically insulating material within at least a portion of the aperture in the electrochemical cell compartment.

In Example 58, the subject matter of any one or any combination of Examples 1-57 may optionally be configured such that the method includes thermally sealing the electrically insulating material, such as by providing energy to the electrically insulating material.

In Example 59, the subject matter of any one or any combination of Examples 1-58 may optionally be configured such that the method includes laser welding the electrically conducting pin to the electrically conducting pad.

In Example 60, the subject matter of any one or any combination of Examples 1-59 may optionally be configured such that the electrically insulating material may include a washer including a washer aperture. Disposing the electrically insulating material may include positioning the washer between the electrically conducting pad and the electrochemical cell compartment such that the washer aperture and the aperture in the electrochemical cell compartment are aligned.

In Example 61, the subject matter of any one or any combination of Examples 1-60 may optionally be configured such that disposing the electrically insulating material may include dispensing additional electrically insulating material within at least a portion of the washer aperture.

These examples may be combined in any permutation or combination.

Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

Various aspects of the disclosure have been described. These and other aspects are within the scope of the following claims.

What is claimed is:

1. An implantable medical device comprising:
an electrochemical cell compartment housing defining a barrier between an inside of an electrochemical cell compartment and an outside of the electrochemical cell compartment;
an electrically conducting pad;
an electrically conducting pin electrically coupled to the conducting pad, wherein the electrically conducting pad includes a top side and a bottom side, wherein the electrically conducting pin extends from the bottom side of the conducting pad, wherein the electrically conducting pad is positioned outside of the electrochemical cell compartment and the electrically conducting pin extends through an aperture in the electrochemical cell compartment housing from the inside of the electrochemical cell compartment to the electrically conducting pad positioned on the outside of the electrochemical cell compartment; and
an electrically insulating material surrounding the aperture and located between the bottom side of the electrically insulating pad and the electrochemical cell compartment housing, and wherein the electrically insulating material is configured to insulate the electrically conducting pad from the electrochemical cell compartment housing and form a seal between the inside of the electrochemical cell compartment and the outside of the electrochemical cell compartment.

2. The implantable medical device of claim 1, wherein the seal comprises a hermetic seal between the inside of the electrochemical cell compartment and the outside of the electrochemical cell compartment.

3. The implantable medical device of claim 1, wherein the electrically insulating material is positioned within at least a portion of the aperture in the electrochemical cell compartment housing.

4. The implantable medical device of claim 1, wherein the aperture is substantially vacant of the electrically insulating material.

5. The implantable medical device of claim 1, wherein the electrically insulating material includes a washer positioned between the electrically conducting pad and the electrochemical cell compartment housing, wherein the washer includes a washer aperture, and wherein the electrically conducting pin extends through the washer aperture and through the aperture in the electrochemical cell compartment housing.

6. The implantable medical device of claim 1, wherein the electrically insulating material is configured to be thermally sealed.

7. The implantable medical device of claim 1, wherein the electrically conducting pad is coupled to the electrically conducting pin by a laser welded joint.

8. The implantable medical device of claim 1, wherein the outside of the electrochemical cell compartment comprises one of an electronics compartment, outside of the implantable medical device, or a compartment inside the implantable medical device.

9. The implantable medical device of claim 1, wherein the electrochemical cell compartment houses at least one of an electrochemical cell, or a capacitor.

10. The implantable medical device of claim 1, wherein the electrically insulating material comprises a frit.

11. The implantable medical device of claim 10, wherein the frit comprises a reflowed glass frit material.

12. The implantable medical device of claim 10, wherein the frit comprises low temperature reflow.

13. The implantable medical device of claim 1, wherein the electrically insulating material comprises a plastic.

14. The implantable medical device of claim 13, wherein the plastic comprises a thermoplastic seal.

15. The implantable medical device of claim 13, wherein the plastic comprises an acid modified polypropylene.

16. The implantable medical device of claim 1, wherein the electrically insulating material comprises an epoxy.

17. The implantable medical device of claim 1, wherein the electrochemical cell compartment housing comprises a metal housing.

18. The implantable medical device of claim 17, wherein the metal housing comprises a titanium metal housing.

19. The implantable medical device of claim 1, wherein the electrochemical cell compartment housing comprises a titanium battery enclosure.

20. The implantable medical device of claim 1, wherein a wall thickness of the electrochemical cell compartment is about 0.005 inches to about 0.015 inches.

21. The implantable medical device of claim 1, wherein a wall thickness of the electrochemical cell compartment housing is substantially uniform.

22. The implantable medical device of claim 1, wherein a thickness of the electrically conducting pad between the top and bottom surface is about 0.003 inches to about 0.008 inches.

23. The implantable medical device of claim 1, wherein the electrically insulating material includes an insulating layer, and wherein a thickness of the insulating layer between the electrically conducting pad and the electrochemical cell compartment housing is about 0.003 inches to about 0.010 inches.

24. The implantable medical device of claim 1, wherein the electrically insulating material includes an insulating layer, and wherein a thickness of the cover portion, the insulating layer, and the electrically conducting pad combined is about 0.015 inches to about 0.020 inches.

25. The implantable medical device of claim 1, further comprising an electrochemical cell in the inside of the electrochemical cell compartment, wherein the electrically conducting pin is connected to a first polarity of the electrochemical cell in the inside the electrochemical cell compartment.

26. The implantable medical device of claim 25, further comprising electronics outside electrochemical cell compartment housing, the electronics connected to the first polarity of the electrochemical cell via the electrically conducting pad and the electrically conducting pin such that the electrochemical cell supplies operating power to the electronics.

27. A method for manufacturing an implantable medical device including electrochemical cell compartment housing defining a barrier between an inside of an electrochemical cell compartment and an outside of the electrochemical cell compartment, the method comprising:
    positioning an electrically conducting pin to extend through an aperture in the electrochemical cell compartment housing, wherein the electrically conducting pin is electrically coupled to an electrically conducting pad including a top side and a bottom side, wherein the electrically conducting pad is positioned outside of the electrochemical cell compartment,
    disposing an electrically insulating material surrounding the aperture and between the bottom side of the electrically conducting pad and the electrochemical cell compartment housing, wherein the electrically insulating material is configured to insulate the electrically conducting pad from the electrochemical cell compartment housing and form a seal between the inside of the electrochemical cell compartment and the outside of the electrochemical cell compartment.

28. The method of claim 27, further comprising disposing the electrically insulating material within at least a portion of the aperture in the electrochemical cell compartment housing.

29. The method of claim 27, further comprising thermally sealing the electrically insulating material by providing energy to the electrically insulating material.

30. The method of claim 27, further comprising laser welding the electrically conducting pin to the electrically conducting pad.

31. The method of claim 27, wherein the electrically insulating material includes a washer including a washer aperture, wherein disposing the electrically insulating material includes positioning the washer between the electrically conducting pad and the electrochemical cell compartment housing such that the washer aperture and the aperture in the electrochemical cell compartment housing are aligned.

32. The method of claim 31, wherein disposing the electrically insulating material includes dispensing additional electrically insulating material within at least a portion of the washer aperture.

* * * * *